(12) United States Patent
Crea

(10) Patent No.: US 9,012,369 B2
(45) Date of Patent: Apr. 21, 2015

(54) LOOK-THROUGH MUTAGENESIS FOR DEVELOPING ALTERED POLYPEPTIDES WITH ENHANCED PROPERTIES

(75) Inventor: Roberto Crea, Foster City, CA (US)

(73) Assignee: Pfizer Inc., New York, NY (US)

( * ) Notice: Subject to any disclaimer, the term of this patent is extended or adjusted under 35 U.S.C. 154(b) by 2184 days.

(21) Appl. No.: 11/571,088

(22) PCT Filed: Jul. 6, 2005

(86) PCT No.: PCT/US2005/024140
§ 371 (c)(1),
(2), (4) Date: Jan. 10, 2008

(87) PCT Pub. No.: WO2006/023144
PCT Pub. Date: Mar. 2, 2006

(65) Prior Publication Data
US 2008/0214406 A1 Sep. 4, 2008

Related U.S. Application Data

(60) Provisional application No. 60/585,918, filed on Jul. 6, 2004.

(51) Int. Cl.
C40B 30/04 (2006.01)
C12N 15/10 (2006.01)
C07K 16/00 (2006.01)
C07K 16/18 (2006.01)
G01N 33/68 (2006.01)

(52) U.S. Cl.
CPC .............. *C12N 15/102* (2013.01); *C07K 16/00* (2013.01); *C07K 16/18* (2013.01); *C07K 2317/565* (2013.01); *C07K 2317/622* (2013.01); *C07K 2317/92* (2013.01); *C12N 15/1093* (2013.01); *G01N 33/6854* (2013.01); *G01N 33/6857* (2013.01)

(58) Field of Classification Search
None
See application file for complete search history.

(56) References Cited

FOREIGN PATENT DOCUMENTS

| WO | WO91/15581 | 10/1991 |
|---|---|---|
| WO | WO01/32712 | 5/2001 |
| WO | WO01/44463 | 6/2001 |
| WO | WO03/023032 | 3/2003 |

(Continued)

OTHER PUBLICATIONS

Adams (1999) Journal of Immunological Methods vol. 231 pp. 249 to 260.*

(Continued)

*Primary Examiner* — Christian Boesen
(74) *Attorney, Agent, or Firm* — Pfizer Inc.

(57) ABSTRACT

A method of mutagenesis by which a predetermined amino acid is introduced into each and every position of a selected set of positions in a preselected region (or several different regions) of a polypeptide to produce a library of polypeptide analogs is disclosed. The method is based on the premise that certain amino acids play a crucial role in the structure and function of proteins and thus is capable of identifying and distinguishing functional amino acid residues ("hot spots") from non-functional amino acids residues ("cold spots") within a polypeptide or portion thereof. Libraries can be generated which contain only desired polypeptide analogs and are of reasonable size for screening. The libraries can be used to study the role of specific amino acids in polypeptide structure and function and to develop new or improved polypeptides such as antibodies, antibody fragments, single chain antibodies, enzymes, and ligands.

14 Claims, 15 Drawing Sheets

(56) References Cited

FOREIGN PATENT DOCUMENTS

| | | |
|---|---|---|
| WO | WO03/088911 | 10/2003 |
| WO | WO03/089671 | 10/2003 |
| WO | WO2005/003345 | 1/2005 |

OTHER PUBLICATIONS

Adams (Dec. 10, 1999) Journal of Immunological Methods vol. 231 pp. 249 to 260.*

Schier et al. (Nov. 8, 1996) Journal of Molecular Biology vol. 263 pp. 551 to 567.*

Auger et al. (Mar. 19, 2002) European Journal of Immunology vol. 32 pp. 1052 to 1058.*

Cunningham, High-Resolution Epitope Mapping of High-Receptor Interactions by Alanine-Scanning Matagenesis, Science 1989, V244, p. 1081-85.

Adams, et al., Generating improved single-chain Fv molecules for tumor targeting, J of Immunological Methods, 1999, V231, p. 249-60.

Wang, J., Survey and Summary from DNA biosensors to gene chips, Nucleic Acids Research, 2000, V28, p. 3011-16.

Glokler, et al., Protein and antibody microarray technology, J of Chromatography B, 2003, V797, p. 229-40.

Shultz, et al., Site-saturation studies of beta-lactamase:productions and characterization of mutant . . . Proceedings of Nat. Acad. of Sciences, 1986 V83, p. 1588-92.

* cited by examiner

Matrix showing combined light and heavy chain CDR mutagenesis permutations

|       | 000 | 100 | 010 | 001 | 110 | 101 | 011 | 111 |
|-------|-----|-----|-----|-----|-----|-----|-----|-----|
| 000   |     | 1   | 1   | 1   | 2   | 2   | 2   | 3   |
| 100   | 1   | 2   | 2   | 2   | 3   | 3   | 3   | 4   |
| 010   | 1   | 2   | 2   | 2   | 3   | 3   | 3   | 4   |
| 001   | 1   | 2   | 2   | 2   | 3   | 3   | 3   | 4   |
| 110   | 2   | 3   | 3   | 3   | 4   | 4   | 4   | 5   |
| 101   | 2   | 3   | 3   | 3   | 4   | 4   | 4   | 5   |
| 011   | 2   | 3   | 3   | 3   | 4   | 4   | 4   | 5   |
| 111   | 3   | 4   | 4   | 4   | 5   | 5   | 5   | 6   | heavy chain CDRs (columns); light chain CDRs (rows)

*Fig. 5*

Schematic of single chain antibody (scFv) yeast expression, display, and screening cassette

Fig. 14

SEQUENCE LISTING

<160> NUMBER OF SEQ ID NOS: 134

<210> SEQ ID NO 1
<211> LENGTH: 399
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 1
atgaaatacc tattgcctac ggcggccgct ggattgttat tactcgctgc ccaaccagcc      60
atggccgaca ttgtgctgac ccaatctcca gcttctttgg ctgtgtctct agggcagagg     120
gccaccatat cctgcagagc cagtgaaagt gttgatagtt atggcaatag ttttatgcac     180
tggtaccagc agaaaccagg acagccaccc aaactcctca tctatcttgc atccaaccta     240
gaatctgggg tccctgccag gttcagtggc agtgggtcta ggacagactt caccctcacc     300
attgatcctg tggaggctga tgatgctaca acctattact gtcagcaaaa taatgaggat     360
ccattcacgt tcggctcggg gacaaagttg gaaataaaa                             399

<210> SEQ ID NO 2
<211> LENGTH: 429
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 2
gtgaaacaaa gcactattgc actggcactc ttaccgttac tgtttacccc tgtgacaaaa      60
gcccaggtcc aactgcagca gtctggacct gagctggtga agcctggggc ttcagtgaag     120 atacccctgca aggcttctgg atacacattc actgactaca catggactg gtgaagcag      180 agccatggaa agagccttga gtggattgga gatattaatc ctagcaatgg ttatactatc     240
tacaaccaga agttcaaggg caaggccaca ttgactgtag acaagtcctc agcacagcc      300 tacatggagc tccgcagcct gacatctgag gacactgcag tctattactg tgcaagatca     360
gggtacggct cacgacatcc gcctgggttt gcttactggg gccaagggac tctggtcact     420
gtctctgca                                                             429

<210> SEQ ID NO 3
<211> LENGTH: 132
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Asp Ile Val Leu Thr Gln Ser Pro Ala Ser
            20                  25                  30

Leu Ala Val Ser Leu Gly Gln Arg Ala Thr Ile Ser Cys Arg Ala Ser
        35                  40                  45

Glu Ser Val Asp Ser Tyr Gly Asn Ser Phe Met His Trp Tyr Gln Gln
    50                  55                  60

Lys Pro Gly Gln Pro Pro Lys Leu Leu Ile Tyr Leu Ala Ser Asn Leu
65                  70                  75                  80

Glu Ser Gly Val Pro Ala Arg Phe Ser Gly Ser Gly Ser Arg Thr Asp
                85                  90                  95

Phe Thr Leu Thr Ile Asp Pro Val Glu Ala Asp Ala Thr Thr Tyr
            100                 105                 110

Tyr Cys Gln Gln Asn Asn Glu Asp Pro Phe Thr Phe Gly Thr Lys
        115                 120                 125

Leu Glu Ile Lys
    130

<210> SEQ ID NO 4
<211> LENGTH: 143
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 4

Val Lys Gln Ser Thr Ile Ala Leu Ala Leu Leu Pro Leu Leu Phe Thr
1               5                   10                  15

Pro Val Thr Lys Ala Gln Val Gln Leu Gln Gln Ser Gly Pro Glu Leu
            20                  25                  30

Val Lys Pro Gly Ala Ser Val Lys Ile Pro Cys Lys Ala Ser Gly Tyr
        35                  40                  45

Thr Phe Thr Asp Tyr Asn Met Asp Trp Val Lys Gln Ser His Gly Lys
    50                  55                  60

Ser Leu Glu Trp Ile Gly Asp Ile Asn Pro Ser Asn Gly Tyr Thr Ile
65                  70                  75                  80

Tyr Asn Gln Lys Phe Lys Gly Lys Ala Thr Leu Thr Val Asp Lys Ser
                85                  90                  95

Ser Ser Thr Ala Tyr Met Glu Leu Arg Ser Leu Thr Ser Glu Asp Thr
            100                 105                 110

Ala Val Tyr Tyr Cys Ala Arg Ser Gly Tyr Gly Ser Arg His Pro Pro
        115                 120                 125

Gly Phe Ala Tyr Trp Gly Gln Gly Thr Leu Val Thr Val Ser Ala
    130                 135                 140

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Glu Ser Val Asp Ser Tyr Gly Asn Ser Phe Met His
1               5                   10                  15

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Ala Ser Asn Leu Glu Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Asn Asn Glu Asp Pro Phe Thr
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Tyr Asn Met Asp
  1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Ile Asn Pro Ser Asn Gly Tyr Thr Ile Tyr Asn Gln Lys Phe Lys
  1               5                  10                  15

Gly

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Gly Tyr Gly Ser Arg His Pro Pro Gly Phe Ala Tyr
  1               5                  10

<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggtggaggcg gttctggtgg aggcggttcg ggtggcggag gttcaaaata cctattgcct    60
acggcagcgg ctgg                                                      74

<210> SEQ ID NO 12
<211> LENGTH: 39
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 12
tttccttttt gcggccgctt ttatttccaa ctttgtccc                    39

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccggaattca tggtgaaaca aagcactatt gcactg                       36

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgaacctccg ccacccgaac cgcctccacc agaaccgcct ccacctgcag agacagtgac   60
cag                                                           63

<210> SEQ ID NO 15
<211> LENGTH: 268
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 15

Gln Val Gln Leu Gln Gln Ser Gly Pro Glu Leu Val Lys Pro Gly Ala
  1               5                  10                  15

Ser Val Lys Ile Pro Cys Lys Ala Ser Gly Tyr Thr Phe Thr Asp Tyr
                 20                  25                  30

Asn Met Asp Trp Val Lys Gln Ser His Gly Lys Ser Leu Glu Trp Ile
             35                  40                  45

Gly Asp Ile Asn Pro Ser Asn Gly Tyr Thr Ile Tyr Asn Gln Lys Phe
         50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Thr Ala Val Tyr Tyr Cys
                 85                  90                  95

Ala Arg Ser Gly Tyr Gly Ser Arg His Pro Pro Gly Phe Ala Tyr Trp
            100                 105                 110

Gly Gln Gly Thr Leu Val Thr Val Ser Ser Gly Gly Gly Gly Ser Gly
            115                 120                 125

Gly Gly Gly Ser Gly Gly Gly Gly Ser Asp Ile Val Leu Thr Gln Ser
        130                 135                 140

Pro Ala Ser Leu Ala Val Ser Leu Gly Gln Arg Ala Thr Ile Ser Cys
145                 150                 155                 160

Arg Ala Ser Glu Ser Val Asp Ser Tyr Gly Asn Ser Phe Met His Trp
                165                 170                 175

Tyr Gln Gln Lys Pro Gly Gln Pro Pro Lys Leu Leu Ile Tyr Leu Ala
            180                 185                 190

Ser Asn Leu Glu Ser Gly Val Pro Ala Arg Phe Ser Gly Ser Gly Ser
        195                 200                 205

Arg Thr Asp Phe Thr Leu Thr Ile Asp Pro Val Glu Ala Asp Asp Ala
    210                 215                 220

Thr Thr Tyr Tyr Cys Gln Gln Asn Asn Glu Asp Pro Phe Thr Phe Gly
225                 230                 235                 240

Ser Gly Thr Lys Leu Glu Ile Lys Ala Ala Ala His His His His
            245                 250                 255

His Gly Glu Gln Lys Leu Ile Ser Glu Glu Asp Leu
        260                 265

<210> SEQ ID NO 16
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agccttgagt ggattggaga tattaatcct agcaatggtt atactatcta caaccagaag    60
ttcaagggca aggccacatt gactgtagac                                     90

<210> SEQ ID NO 17
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agccttgagt ggattggatt gattaatcct agcaatggtt atactatcta caaccagaag    60
ttcaagggca aggccacatt gactgtagac                                     90

<210> SEQ ID NO 18
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
agccttgagt ggattggaga tttgaatcct agcaatggtt atactatcta caaccagaag    60
ttcaagggca aggccacatt gactgtagac                                     90

<210> SEQ ID NO 19
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agccttgagt ggattggaga tattttgcct agcaatggtt atactatcta caaccagaag    60
ttcaagggca aggccacatt gactgtagac                                     90

-continued

```
<210> SEQ ID NO 20
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agccttgagt ggattggaga tattaatttg agcaatggtt atactatcta caaccagaag      60
ttcaagggca aggccacatt gactgtagac                                        90

<210> SEQ ID NO 21
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agccttgagt ggattggaga tattaatcct ttgaatggtt atactatcta caaccagaag      60
ttcaagggca aggccacatt gactgtagac                                        90

<210> SEQ ID NO 22
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agccttgagt ggattggaga tattaatcct agcttgggtt atactatcta caaccagaag      60
ttcaagggca aggccacatt gactgtagac                                        90

<210> SEQ ID NO 23
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agccttgagt ggattggaga tattaatcct agcaatttgt atactatcta caaccagaag      60
ttcaagggca aggccacatt gactgtagac                                        90

<210> SEQ ID NO 24
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agccttgagt ggattggaga tattaatcct agcaatggtt tgactatcta caaccagaag      60
ttcaagggca aggccacatt gactgtagac                                        90

<210> SEQ ID NO 25
<211> LENGTH: 90
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 25
agccttgagt ggattggaga tattaatcct agcaatggtt atttgatcta caaccagaag    60
ttcaagggca aggccacatt gactgtagac                                     90

<210> SEQ ID NO 26
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agccttgagt ggattggaga tattaatcct agcaatggtt atactttgta caaccagaag    60
ttcaagggca aggccacatt gactgtagac                                     90

<210> SEQ ID NO 27
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
agccttgagt ggattggaga tattaatcct agcaatggtt atactatctt gaaccagaag    60
ttcaagggca aggccacatt gactgtagac                                     90

<210> SEQ ID NO 28
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agccttgagt ggattggaga tattaatcct agcaatggtt atactatcta cttgcagaag    60
ttcaagggca aggccacatt gactgtagac                                     90

<210> SEQ ID NO 29
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agccttgagt ggattggaga tattaatcct agcaatggtt atactatcta caacttgaag    60
ttcaagggca aggccacatt gactgtagac                                     90

<210> SEQ ID NO 30
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 30
agccttgagt ggattggaga tattaatcct agcaatggtt atactatcta caaccagttg     60
ttcaagggca aggccacatt gactgtagac                                      90

<210> SEQ ID NO 31
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
agccttgagt ggattggaga tattaatcct agcaatggtt atactatcta caaccagaag     60
ttgaagggca aggccacatt gactgtagac                                      90

<210> SEQ ID NO 32
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agccttgagt ggattggaga tattaatcct agcaatggtt atactatcta caaccagaag     60
ttcttgggca aggccacatt gactgtagac                                      90

<210> SEQ ID NO 33
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
agccttgagt ggattggaga tattaatcct agcaatggtt atactatcta caaccagaag     60
ttcaagttga aggccacatt gactgtagac                                      90

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgaaacaaa gcactattgc actggcactc ttaccgtta                            39

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tccattccac tcaaggctct ttccatggct ctgcttcacc aa                        42

<210> SEQ ID NO 36
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ttttatttcc aactttgtcc ccgcgcc                                          27

<210> SEQ ID NO 37
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtcagtgaat gtgtatccag aagccttgca gggtat                                36

<210> SEQ ID NO 38
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcttctggat acacattcac tcactacaac atggactggg tgaagcagag ccatgga         57

<210> SEQ ID NO 39
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcttctggat acacattcac tgaccacaac atggactggg tgaagcagag ccatgga         57

<210> SEQ ID NO 40
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcttctggat acacattcac tgactaccac atggactggg tgaagcagag ccatgga         57

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gcttctggat acacattcac tgactacaac atgcactggg tgaagcagag ccatgga         57

<210> SEQ ID NO 42
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Leu Glu Trp Ile Gly Asp Ile Asn Pro Ser Asn Gly Tyr Thr Ile
 1               5                  10                  15

Tyr Asn Gln Lys Phe Lys Gly Phe Lys Gly Lys Ala Thr Leu
            20                  25                  30

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Leu Glu Trp Ile Gly
 1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Ala Thr Leu Thr Val Asp
 1               5

<210> SEQ ID NO 45
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
agccttgagt ggattggaga tattaatcct agcaatggtt atactatcta caaccagaag      60
ttcaagggct tcaagggcaa ggccacattg                                       90

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
raswaswacm wssmcwrg                                                    18

<210> SEQ ID NO 47
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 47

Asp Ile Asn Pro Ser Asn Gly Tyr Thr Ile Tyr Asn Gln Lys
 1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Leu Ile Asn Pro Ser Asn Gly Tyr Thr Ile Tyr Asn Gln Lys
 1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Leu Asn Pro Ser Asn Gly Tyr Thr Ile Tyr Asn Gln Lys
 1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Ile Leu Pro Ser Asn Gly Tyr Thr Ile Tyr Asn Gln Lys
 1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Ile Asn Leu Ser Asn Gly Tyr Thr Ile Tyr Asn Gln Lys
 1               5                   10

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Ile Asn Pro Leu Asn Gly Tyr Thr Ile Tyr Asn Gln Lys
 1               5                   10

<210> SEQ ID NO 53
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 53

Asp Ile Asn Pro Ser Leu Gly Tyr Thr Ile Tyr Asn Gln Lys
 1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ile Asn Pro Ser Asn Leu Tyr Thr Ile Tyr Asn Gln Lys
 1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Ile Asn Pro Ser Asn Gly Leu Thr Ile Tyr Asn Gln Lys
 1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Ile Asn Pro Ser Asn Gly Tyr Leu Ile Tyr Asn Gln Lys
 1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ile Asn Pro Ser Asn Gly Tyr Thr Leu Tyr Asn Gln Lys
 1               5                   10

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ile Asn Pro Ser Asn Gly Tyr Thr Ile Leu Asn Gln Lys
 1               5                   10
```

```
<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ile Asn Pro Ser Asn Gly Tyr Thr Ile Tyr Leu Gln Lys
 1               5                  10

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Asp Ile Asn Pro Ser Asn Gly Tyr Thr Ile Tyr Asn Leu Lys
 1               5                  10

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Ile Asn Pro Ser Asn Gly Tyr Thr Ile Tyr Asn Gln Leu
 1               5                  10

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
catctcaccc aaagacgctc t                                            21

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 63

His His His His His His
 1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 64

Asp Tyr Asn Met Asp Trp
 1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Tyr Asn Met Asp Trp
 1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Asp Lys Asn Met Asp Trp
 1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Tyr Tyr Met Asp Trp
 1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Tyr Asn His Asp Trp
 1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asp Tyr Asn Lys Asp Trp
 1               5

<210> SEQ ID NO 70
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 70

Asp Tyr Asn Met Pro Trp
 1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Asp Tyr Asn Met Asp Lys
 1               5

<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Asp Ile Asn Pro Ser Asn Gly Tyr Thr Ile Tyr Asn Gln Lys
 1               5                  10

<210> SEQ ID NO 73
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Ile Asn Pro Ser Asn Gly Tyr Thr Ile Tyr Asn Gln Lys
 1               5                  10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Ile Asn Pro Ser Asn Gly Tyr Thr Ile Tyr Asn Gln Lys
 1               5                  10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Ile Asn Lys Ser Asn Gly Tyr Thr Ile Tyr Asn Gln Lys
 1               5                  10
```

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Asp Ile Asn Pro Lys Asn Gly Tyr Thr Ile Tyr Asn Gln Lys
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asp Ile Asn Pro Ser Ser Gly Tyr Thr Ile Tyr Asn Gln Lys
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ile Asn Pro Ser Ala Gly Tyr Thr Ile Tyr Asn Gln Lys
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ile Asn Pro Ser Asn Gly Ala Thr Ile Tyr Asn Gln Lys
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ile Asn Pro Ser Asn Gly His Thr Ile Tyr Asn Gln Lys
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Ile Asn Pro Ser Asn Gly Lys Thr Ile Tyr Asn Gln Lys
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Ile Asn Pro Ser Asn Gly Tyr Leu Ile Tyr Asn Gln Lys
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Ile Asn Pro Ser Asn Gly Tyr Thr Pro Tyr Asn Gln Lys
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Ile Asn Pro Ser Asn Gly Tyr Thr Ile Lys Asn Gln Lys
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ile Asn Pro Ser Asn Gly Tyr Thr Ile His Asn Gln Lys
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Ile Asn Pro Ser Asn Gly Tyr Thr Ile Tyr Lys Gln Lys
1               5                   10

<210> SEQ ID NO 87
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Ile Asn Pro Ser Asn Gly Tyr Thr Ile Tyr Asn Pro Lys
 1               5                  10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ile Asn Pro Ser Asn Gly Tyr Thr Ile Tyr Asn His Lys
 1               5                  10

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Ile Asn Pro Ser Asn Gly Tyr Thr Ile Tyr Asn Gln Leu
 1               5                  10

<210> SEQ ID NO 90
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Ile Asn Pro Ser Asn Gly Tyr Thr Ile Tyr Asn Gln Gln
 1               5                  10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ser Gly Tyr Gly Ser Arg His Pro Pro Gly Phe Ala
 1               5                  10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Gly Tyr Gly Ser Arg His Pro Pro Gly Phe Ala
```

```
                    1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Gly Tyr Gly Ser Arg His Pro Pro Gly Phe Ala
  1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Leu Gly Tyr Gly Ser Arg His Pro Pro Gly Phe Ala
  1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ser Lys Tyr Gly Ser Arg His Pro Pro Gly Phe Ala
  1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Gly Tyr Lys Ser Arg His Pro Pro Gly Phe Ala
  1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Tyr Gly Ser Arg Gln Pro Pro Gly Phe Ala
  1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 98

Ser Gly Tyr Gly Ser Arg His Leu Pro Gly Phe Ala
 1               5                  10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ser Gly Tyr Gly Ser Arg His Gln Pro Gly Phe Ala
 1               5                  10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ser Gly Tyr Gly Ser Arg His Pro His Gly Phe Ala
 1               5                  10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Gly Tyr Gly Ser Arg His Pro Gln Gly Phe Ala
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Gly Tyr Gly Ser Arg His Pro Pro Ser Phe Ala
 1               5                  10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ser Gly Tyr Gly Ser Arg His Pro Pro Lys Phe Ala
 1               5                  10

<210> SEQ ID NO 104

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Gly Tyr Gly Ser Arg His Pro Pro Gly His Ala
 1               5                  10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ser Gly Tyr Gly Ser Arg His Pro Pro Gly Gln Ala
 1               5                  10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Ala Ser Glu Ser Val Asp Ser Tyr Gly Asn
 1               5                  10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala His Glu Ser Val Asp Ser Tyr Gly Asn
 1               5                  10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Ser Leu Ser Val Asp Ser Tyr Gly Asn
 1               5                  10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109
```

Arg Ala Ser Glu Asp Val Asp Ser Tyr Gly Asn
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ala Ser Glu Ser Val Lys Ser Tyr Gly Asn
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ala Ser Glu Ser Val Ser Ser Tyr Gly Asn
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ala Ser Glu Ser Val Tyr Ser Tyr Gly Asn
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Ala Ser Glu Ser Val Asp Leu Tyr Gly Asn
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Glu Ser Val Asp Lys Tyr Gly Asn
1               5                   10

<210> SEQ ID NO 115
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 115

Arg Ala Ser Glu Ser Val Asp Ser Asp Gly Asn
  1               5                  10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Ala Ser Glu Ser Val Asp Ser Pro Gly Asn
  1               5                  10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ala Ser Glu Ser Val Asp Ser Tyr Ala Asn
  1               5                  10

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Leu Ala Ser Asn Leu
  1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Tyr Ala Ser Asn Leu
  1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gln Ala Ser Asn Leu
  1               5
```

```
<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Leu Leu Ser Asn Leu
 1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Leu Ala His Asn Leu
 1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Leu Ala Ser Asn Ala
 1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Leu Ala Ser Asn Ser
 1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gln Asn Asn Glu Asp Pro Glu Thr
 1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126
```

```
Lys Gln Asn Asn Glu Asp Pro Glu Thr
 1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gln Pro Asn Asn Glu Asp Pro Glu Thr
 1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Gln Leu Asn Glu Asp Pro Glu Thr
 1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gln Gln Gln Asn Glu Asp Pro Glu Thr
 1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gln Gln Asn Pro Glu Asp Pro Glu Thr
 1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gln Gln Asn Asn Glu Asp Leu Glu Thr
 1               5

<210> SEQ ID NO 132
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 132

Gln Gln Asn Asn Glu Asp Pro Pro Thr
 1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Gln Asn Asn Glu Asp Pro Glu Ala
 1               5

<210> SEQ ID NO 134
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gcttctggat acacattcac tgactacaac cacgactggg tgaagcagag ccatgga         57
```

LOOK-THROUGH MUTAGENESIS FOR DEVELOPING ALTERED POLYPEPTIDES WITH ENHANCED PROPERTIES

This application is the U.S. National Stage Entry under 35 U.S.C. §371 of International Application No. PCT/US05/24140, filed Jul. 6, 2005, which claims the benefit of U.S. Provisional Application No. 60/585,918, filed Jul. 6, 2004, each of which is hereby incorporated by reference in its entirety.

RELATED INFORMATION

The entire contents of all other patents, patent applications, and references cited throughout the following specification also are incorporated by reference herein in their entireties.

BACKGROUND OF THE INVENTION

Mutagenesis is a powerful tool in the study of protein structure and function. Mutations can be made in the nucleotide sequence of a cloned gene encoding a protein of interest and the modified gene can be expressed to produce mutants of the protein. By comparing the properties of a wild-type protein and the mutants generated, it is often possible to identify individual amino acids or domains of amino acids that are essential for the structural integrity and/or biochemical function of the protein, such as its binding and/or catalytic activity. The number of mutants that can be generated from a single protein, however, renders it difficult to select mutants that will be informative or have a desired property, even if the selected mutants that encompass the mutations are solely in putatively important regions of a protein (e.g., regions that make up an active site of a protein). For example, the substitution, deletion, or insertion of a particular amino acid may have a local or global effect on the protein.

Previous methods for mutagenizing polypeptides have been either too restrictive, too inclusive, or limited to knocking out protein function rather than to gaining or improving function. For example, a highly restrictive approach is selective or site-directed mutagenesis which is used to identify the presence of a particular functional site or understand the consequences of making a very specified alteration within the functional site. A common application of site directed mutagenesis is in the study of phosphoproteins where an amino acid residue, that would ordinarily be phosphorylated and allow the polypeptide to carry out its function, is altered to confirm the link between phosphorylation and functional activity. This approach is very specific for the polypeptide and residue being studied.

Conversely, a highly inclusive approach is saturation or random mutagenesis that is designed to produce a large number of mutations encompassing all possible alterations within a defined region of a gene or protein. This is based on the principle that, by generating essentially all possible variants of a relevant protein domain, the proper arrangement of amino acids is likely to be produced as one of the randomly generated mutants. However, in practice, the vast number of random combinations of mutations generated can prevent the capacity to meaningfully select a desired candidate because of the presence of the so-called "noise" of so many undesired candidates.

Another approach, referred to as "Walk Through" mutagenesis (see, e.g., U.S. Pat. Nos. 5,830,650; 5,798,208) has been used to mutagenize a defined region of a polypeptide by synthesizing a mixture of degenerate oligonucleotides that, statistically, contain a desired set of mutations. However, because degenerate polynucleotide synthesis is employed, Walk-Through mutagenesis yields a number of undesired alterations in addition to the desired set of mutations. For example, to sequentially introduce a mutation across a defined region of only five amino acid positions, a set of over 100 polynucleotide must be made (and screened) (see, e.g., FIG. 6). Accordingly, to make and screen, for example, two or three regions becomes increasingly complex, i.e., requiring the making and screening of 200 to over 300 polynucleotides, respectively, for the presence of only 10 to 15 mutations.

In yet another approach which has been used to mutagenize proteins is alanine scanning mutagenesis, where an alanine residue is "scanned" through a portion of a protein to identify positions where the protein's function is interrupted. However, this approach only looks at loss of protein function by way of substituting a neutral alanine residue at a given position, rather than gain or improvement of function. Thus, it is not a useful approach for generating proteins having improved structure and function.

Accordingly, a need remains for a systematic way to mutagenize a protein for new or improved function.

SUMMARY OF THE INVENTION

The invention pertains to a method of mutagenesis for the generation of novel or improved proteins (or polypeptides) and to libraries of polypeptide analogs and specific polypeptides generated by the methods. The polypeptide targeted for mutagenesis can be a natural, synthetic or engineered polypeptide, including fragments, analogs and mutant forms thereof.

In one embodiment, the method comprises introducing a predetermined amino acid into essentially every position within a defined region (or several different regions) of the amino acid sequence of a polypeptide. A polypeptide library is generated containing polypeptide analogs which individually have no more than one predetermined amino acid, but which collectively have the predetermined amino acid in every position within the defined region(s). Alone, this method can be referred to as "look-through" mutagenesis because, in effect, a single, predetermined amino acid (and only the predetermined amino acid) is substituted position-by-position throughout one or more defined region(s) of a polypeptide.

However, in a preferred embodiment, the LTM method is improved by using it to identify functional amino acids (or so-called "hot spots") from non-functional amino acids (or so-called "cold spots") within a polypeptide, or portion thereof, to further reduce the number of residues to be altered in order to screen and obtain a desired property in a polypeptide. Accordingly, the improved method of look-through mutagenesis (LTM) (hereafter the improved LTM being referred to as LTM2) allows for the identification and building of a subset of candidate molecules representing only the most relevant functional alterations in the polypeptide which can then be efficiently screened free of any "noise". Importantly, LTM2 also allows for the construction of an LTM2 library having superior advantages over traditional libraries because it has been designed to include only alterations in the amino acid residues of the polypeptide most likely to have an effect on the function of the polypeptide and therefore, upon screening, more likely to yield an altered polypeptide having an enhanced property. Thus, LTM2 allows one to "look-through" the structural and functional consequences of separately substituting a predetermined amino acid at each functional amino acid position within a defined region of the polypeptide, thereby segregating a specific protein chemistry to the defined region without any interference or "noise" from the generation of unwanted polypeptide analogs (i.e., analogs containing amino acid substitutions other than those that follow the LTM2 scheme) (see, for example, FIG. 1).

Accordingly, the present invention allows for highly efficient and accurate systematic evaluation of the role of a specific amino acid change in one or more defined regions of a polypeptide. This becomes particularly important when evaluating (by mutating) two or more defined regions, such that the number of polypeptide analogs required greatly increases and, thus, the presence of undesired analogs also increases. The present invention obviates this problem by completely eliminating undesired analogs and, thus, the potential that any changes in protein structure or function observed are the result of anything but substitution of the predetermined amino acid. Thus, the effect of segregating a specific protein chemistry to even multiple regions with a protein can be studied with high accuracy and efficiency. Importantly, this includes studying how mutagenesis can effect the interaction of such regions, thereby improving the overall structure and function of the protein.

In a particular embodiment of the invention, the methods of the invention are suitable for identifying a particular chemical motif that maps to one or more functional amino acid resides or positions. The amino acid residue(s) that contribute to such a chemical motif can occur at one or more positions that are contiguous, non-contiguous, within one or more CDR regions, and/or within one or more polypeptides, for example, antibody heavy and light chains. The methods of the invention allow for the further exploration of a chemical motif in that they allow for the systematic testing (or chemical profiling) of related amino acid chemistries at selected amino acid position(s) or defined region(s). Accordingly, in one embodiment, the invention provides a method for identifying a desired chemistry and then exploring the consequences of incorporating related or unrelated chemistries to achieve either an enhanced property or to remove a deleterious property. Typical amino acid side chain chemistries suitable for profiling by the methods of the invention are polar, positively charged, negatively charged, and hydrophobic amino acid side chain chemistries. In one embodiment, a charged chemistry is identified as resident at a selected amino acid reside(s), position, or defined region(s) and other charged amino acids are substituted for the parental amino acid such that an alteration in a measurable property is achieved. In a preferred embodiment, the alteration in a measurable property is an enhanced property in an antibody, for example, improved antigen-binding or effector function.

Accordingly, the invention also provides antibody libraries comprising related amino acid side group chemistries introduced at selected amino acid positions(s)/defined regions having, for example, related chemistry, for the efficient screening of antibodies with improved properties.

In another embodiment of the invention, the library of polypeptide analogs is generated and screened by first synthesizing individual polynucleotides encoding a defined region or regions of a polypeptide where, collectively, the polynucleotides represent all possible variant polynucleotides according to the look-through criteria described herein. The method is used to identify and distinguish functional amino acid residue(s) (positions) from non-functional amino acid residue(s) (positions). A subset of variant polynucleotides are expressed, for example, using in vitro transcription and translation and/or using a display technology, such as ribosome display, phage display, bacterial display, yeast display, arrayed display, or any other suitable display system known in the art.

The expressed polypeptides are then screened and selected using functional assays, such as binding assays or enzymatic/catalytic assays. In one embodiment, the polypeptides are expressed in association with the polynucleotide that encodes the polypeptide, thereby allowing for identification of the polynucleotide sequence that encodes the polypeptide. In yet another embodiment, the polypeptides are directly synthesized using protein chemistry.

In yet another embodiment of the invention, a combinatorial beneficial library of the $V_L$ and $V_H$ CDR amino-acid sequence variations is constructed. This second library is constructed by generating coding sequences having, at each amino acid variation position, codons for the wildtype amino acid and for each of the previously identified beneficial variant amino acids at that position.

Thus, the present invention provides a method of intelligent mutagenesis that can be used to generate libraries of polypeptide analogs that are of a practical size for screening, in part, because the libraries are devoid of any undesired analog polypeptides or so-called noise. The method can be used to study the role of specific amino acids in polypeptide structure and function and to develop new or improved polypeptides such as antibodies, binding fragments or analogs thereof, single chain antibodies, catalytic antibodies, enzymes, and ligands. In addition, the method can be performed with the benefit of a priori information, e.g., via computer modeling, that can be used to select an initial subset of polypeptide analogs to be produced and studied using LTM2.

Other advantages and aspects of the present invention will be readily apparent from the following description and Examples.

BRIEF DESCRIPTION OF THE FIGURES

FIG. 5 illustrates the diversity of the libraries of the invention with the x and y axes of the matrix representing the CDRs of each of the light and heavy chains wherein an "0" indicates a wild-type CDR and a "1" indicates a mutated CDR and the intersected number representing the complexity of the resultant subset library (e.g., 4 means four CDRs are simultaneously mutated).

FIG. 14 shows a matrix representing the functional (hot spots) and non-functional (cold spots) amino acid positions of an exemplary antibody. Mutations associated with enhanced affinity (relative to the reference wild type antibody) based on equilibrium binding ($EC_{50}$) and/or kinetic binding experiments are shown below each $V_H$ and $V_L$ CDR position. Figure discloses SEQ ID NOS 64-133, respectively, in order or appearance.

DETAILED DESCRIPTION OF THE INVENTION

Figure 1:
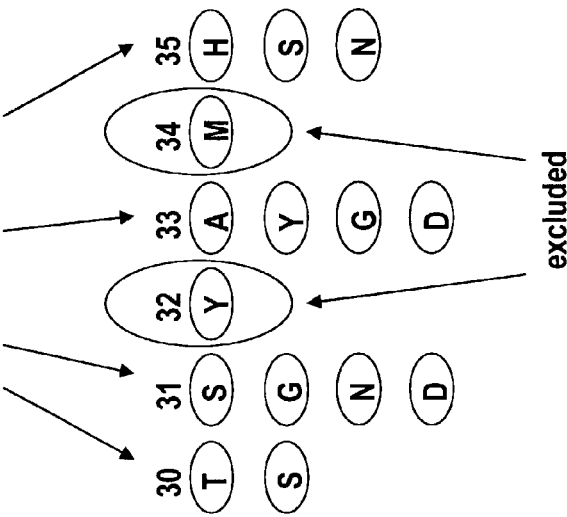
FIG. 1 illustrates the advantages of improved LTM (LTM2) over LTM in that functional amino acids are distinguished from non-functional amino acids such that a more beneficial subset of candidate molecules is obtained and screened.
Figure 1:
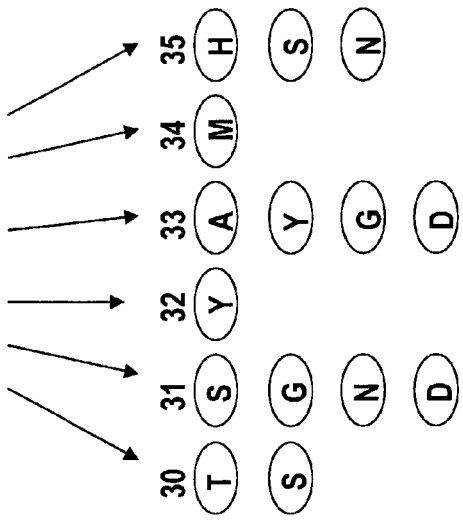

In order to provide a clear understanding of the specification and claims, the following definitions are provided below.

DEFINITIONS

As used herein the term "analog" refers to a variant or mutant polypeptide (or a nucleic acid encoding such a polypeptide) having one or more amino acid substitutions.

The term "binding molecule" refers to any binding molecule, including proteins, polypeptides, and peptides that bind to a substrate or target. In one embodiment, the binding molecule is an antibody or binding fragment thereof (e.g., a Fab fragment), single domain antibody, single chain antibody (e.g., scFv), or peptide capable of binding a ligand. In another embodiment, the binding molecule, in particular, binding molecules comprising CDR region(s), can comprise nontraditional scaffolds or framework regions derived from other antibodies, immunoglobulins, or immunoglobulin-like molecules (e.g., fibronectin), or be in part or in whole, of synthetic origin.

The term "defined region" refers to a selected region of a polypeptide. Typically, the defined region includes all or a portion of a functional site, e.g., the binding site of a ligand, the binding site of a binding molecule or receptor, or a catalytic site. The defined region may also include multiple portions of a functional site. For example, the defined region can include all, a portion, or multiple portions of a complementarity determining region (CDR), e.g., a single domain binding region, or a complete heavy and/or light chain variable region (Fv) of an antibody. Thus, a functional site may include a single or multiple defined regions that contribute to the functional activity of the molecule.

The terms "functional amino acid(s)" and "non-functional amino acid(s)" refer to, respectively, the amino acid residues (or corresponding amino acid residue position) within a polypeptide (or portion thereof) that are determined (using, for example, the methods of the invention) to contribute to a measurable property or activity of the polypeptide. Accordingly, a functional amino acid residue(s) (or corresponding position(s)) is referred to as a "hot spot(s)" as it is a residue or residue position that influences the activity of the polypeptide as compared to a non-functional residue(s) or position(s) which does not influence the activity of the polypeptide and therefore referred to as a "cold spot(s)". A functional amino acid residue (or position) is distinguished from a non-functional amino acid residue (or position) as being suitable for mutagenesis. Typically, when applying the methods of the invention to the investigation of an antibody molecule, amino acid residues that alter, for example, antigen binding, are considered functional residues/positions (i.e., hot spots) whereas residues that do not alter such binding are referred to as non-functional residues/positions (i.e., cold spots).

The term "measurable property" refers to a functional property or activity of a polypeptide (or portion thereof) that can be measured, determined, or assayed for, using standard techniques and include, binding activity, kinase activity, catalytic activity, thermal stability, or enzymatic activity. Measurable properties of polypeptides that are antigen-binding polypeptides, e.g., antibodies, typically include binding specificity, binding avidity, binding affinity, Fc receptor binding, glycosylation, complement binding, half-life stability, solubility, thermal stability, catalytic activity, and enzymatic activity.

The term "look-through mutagenesis" or "LTM" refers to a method for introducing a predetermined amino acid into essentially every position within a defined region (or several different regions) of the amino acid sequence of a polypeptide. A polypeptide library is generated containing polypeptide analogs which individually have no more than one predetermined amino acid, but which collectively have the predetermined amino acid in every position within the defined region(s).

The term "improved look-through mutagenesis" or "LTM2" refers to LTM conducted so as to identify or distinguish functional amino acid residues (hot spots) from non-functional amino acid residues (cold spots). Accordingly, the LTM2 method allows for selectively introducing a predetermined amino acid into the functional amino acid residue positions within a polypeptide (or portion thereof). Corresponding LTM2 libraries are therefore enriched for polypeptides analogs having amino acid alterations most likely to confer an altered or enhanced property. LTM2 can be carried out subsequent to LTM or based on a priori information as to the functionality of a given amino acid residue or residue position.

The term "library" refers to two or more molecules mutagenized according to the method of the invention. The molecules of the library can be in the form of polynucleotides, polypeptides, polynucleotides and polypeptides, polynucleotides and polypeptides in a cell free extract, or as polynucleotides and/or polypeptides in the context of a phage, prokaryotic cells, or in eukaryotic cells. Libraries of the invention can contain 2 or more molecules or polypeptide analogs, for example about 2 to 10, about 10 to 50, about 50 to $10^2$, about $10^3$, about $10^4$, about $10^5$, about $10^6$, about $10^7$, about $10^8$, about $10^9$, about $10^{10}$, about $10^{11}$, about $10^{12}$, about $10^{13}$, or more, or any interval or range of the foregoing.

The term "mutagenizing" refers to the alteration of an amino acid sequence. This can be achieved by altering or producing a nucleic acid (polynucleotide) capable of encoding the altered amino acid sequence, or by the direct synthesis of an altered polypeptide using protein chemistry.

The term "mutagenesis" refers to, unless otherwise specified, any art recognized technique for altering a polynucleotide or polypeptide sequence. Preferred types of mutagenesis include walk-through mutagenesis (WTM), beneficial walk-through mutagenesis, look-through mutagenesis (LTM), improved look-through mutagenesis (LTM2), or combinations thereof.

The term "combinatorial beneficial mutagenesis" refers to a combination library of coding sequences that encode degenerate mixtures of $V_L$ and/or $V_H$ CDR amino-acid sequence variations initially identified from the predetermined LTM amino acid mutagenesis screen as having an alteration on a measurable property. In the combinatorial beneficial mutation approach, oligonucleotide coding sequences are generated which represent combinations of these beneficial mutations identified by LTM. These combinations may be combinations of different beneficial mutations within a single CDR, mutations within two or more CDRs within a single antibody chain, or mutations within the CDRs of different antibody chains.

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase. Typical modifications include methylation, biotinylation, and other art-known modifications. In addition, the nucleic acid molecule can be single-stranded or double-stranded and, where desired, linked or associated (e.g., covalently or non-covalently) to a detectable moiety.

The term "variant polynucleotide" refers to a polynucleotide encoding a corresponding polypeptide analog (or portion thereof) of the invention. Thus, variant polynucleotides contain one or more codons that have been changed to result in expression of a different amino acid.

The term "polypeptide(s)" refers to two or more amino acids joined by a peptide bond, e.g., peptides (e.g., from 2 to ~50 amino acid residues), as well as longer peptide sequences e.g., protein sequences which typically comprises amino acid sequences from as few as 50 amino acid residues to more than 1,000 amino acid residues.

The term "pooling" refers to the combining of polynucleotide variants or polypeptide analogs to form libraries representing the look-through mutagenesis (LTM) or improved look-though mutagenesis (LTM2) of an entire polypeptide region. The molecules may be in the form of a polynucleotide and/or polypeptide and may coexist in the form of a sublibrary, as molecules on a solid support, as molecules in solution, and/or as molecules in one or more organisms (e.g., phage, prokaryotic cells, or eukaryotic cells).

The term "predetermined amino acid" refers to an amino acid residue selected for substitution at each position within a defined region of a polypeptide to be mutagenized. This does not include position(s) within the region that already (e.g., naturally) contain the predetermined amino acid and, thus, which need not be substituted with the predetermined amino acid. Accordingly, each polypeptide analog generated in accordance with the present invention contains no more that one "predetermined amino acid" residue in a given defined region. However, collectively, the library of polypeptide analogs generated contains the predetermined amino acid at each position within the region being mutagenized, and in a preferred embodiment, at amino acid positions determined to be functional (hot spots). Typically, a predetermined amino acid is selected for a particular size or chemistry usually associated with the side group of the amino acid. Suitable predetermined amino acids include, for example, glycine and alanine (sterically small); serine, threonine, and cysteine (nucleophilic); valine, leucine, isoleucine, methionine, and proline (hydrophobic); phenylalanine, tyrosine, and tryptophan (aromatic); aspartate and glutamate (acidic); asparagine, glutamine, and histidine (amide); and lysine and arginine (basic). Use of non-traditional amino acid residues (e.g., homocysteine) are also within the scope of the invention and can be introduced using any art recognized techniques.

DETAILED DESCRIPTION

The study of proteins has revealed that certain amino acids play a crucial role in their structure and function. For example, it appears that only a discrete number of amino acids participate in the binding of an antibody to an antigen or are involved in the catalytic event of an enzyme.

Though it is clear that certain amino acids are critical to the activity or function of proteins, it is difficult to identify which amino acids are involved, how they are involved, and what substitutions can improve the protein's structure or function. In part, this is due to the complexity of the spatial configuration of amino acid side chains in polypeptides and the interrelationship of different portions of the polypeptide that contribute to form a functional site. For example, the interrelationship between the six CDRs of the variable heavy and light chain regions of an antibody contribute to the antigen or ligand-binding pocket.

Previous mutagenesis methods, such as selective (site-directed) mutagenesis and saturation mutagenesis, are of limited utility for the study of protein structure and function in view of the enormous number of possible variations in complex polypeptides. This is especially true given that desirable combinations are often accompanied by the presence of vast amounts of undesirable combinations or so-called noise.

The method of this invention provides a systematic, practical, and highly accurate approach for evaluating the role of particular amino acids and their position, within a defined region of a polypeptide, in the structure or function of the polypeptide and, thus, for producing improved polypeptides.

1. Selecting a Defined Region

In accordance with the present invention, a defined region or regions within a protein are selected for mutagenesis. Typically, the regions are believed to be important to the protein's structure or function. This can be deduced, for example, from what structural and/or functional aspects are known or can be deduced from comparing the defined region(s) to what is known from the study of other proteins, and may be aided by modeling information. For example, the defined region can be one that has a role in a functional site, e.g., in binding, catalysis, or another function. In one embodiment, the defined region is a hypervariable region or complementarity determining region (CDR) of an antigen binding molecule (see, e.g., FIG. 1). In another embodiment, the defined region is a portion of a complementarity determining region (CDR). In other embodiments, two or more defined regions, e.g., CDRs or portions thereof, are selected for mutagenesis.

2. Selecting a Predetermined Amino Acid Residue

The amino acid residue chosen for substitution within the defined region(s) is generally selected from those known to be involved in the structure or function of interest. The twenty naturally occurring amino acids differ with respect to their side chain. Each side chain is responsible for chemical properties that make each amino acid unique. For the purpose of altering binding or creating new binding affinities, any or all of the twenty naturally occurring amino acids generally can be selected, as well as non-traditional amino acid residues (e.g., homocysteine). Thus, previous methods of mutagenesis, which created vast numbers of analogs for every substitution, were impractical for evaluating the effect on protein binding of substitution each of the twenty amino acids. In contrast, the methods of the present invention create a practical number of analogs for each amino acid substitution and, thus, allows for the evaluation of a greater variety of protein chemistries within a segregated region or regions of a protein.

In contrast to protein binding, only a subset of amino acid residues typically participates in enzymatic or catalytic events. For example, from the chemical properties of the side chains, only a selected number of natural amino acids preferentially participate in catalytic events. Such groupings of amino acid side chain chemistries are useful for selecting an appropriate amino acid residue for use in the chemical profiling of a particular amino acid residue or position. These amino acids belong to the group of polar and neutral amino acids such as Ser, Thr, Asn, Gln, Tyr, and Cys, the group of charged amino acids, Asp and Glu, Lys and Arg, and especially the amino acid His. Other polar and neutral side chains are those of Cys, Ser, Thr, Asn, Gln and Tyr. Gly is also considered to be a borderline member of this group. Ser and Thr play an important role in forming hydrogen bonds. Thr has an additional asymmetry at the beta carbon, therefore only one of the stereoisomers is used. The acid amide Gln and Asn can also form hydrogen bonds, the amido groups functioning as hydrogen donors and the carbonyl groups functioning as acceptors. Gln has one more CH2 group than Asn which renders the polar group more flexible and reduces its interaction with the main chain. Tyr has a very polar hydroxyl group (phenolic OH) that can dissociate at high pH values. Tyr behaves somewhat like a charged side chain; its hydrogen bonds are rather strong.

Neutral polar acids are found at the surface as well as inside protein molecules. As internal residues, they usually form hydrogen bonds with each other or with the polypeptide backbone. Cys can form disulfide bridges.

Histidine (His) has a heterocyclic aromatic side chain with a pK value of 6.0. In the physiological pH range, its imidazole ring can be either uncharged or charged, after taking up a hydrogen ion from the solution. Since these two states are readily available, His is quite suitable for catalyzing chemical reactions. It is found in most of the active centers of enzymes, for example, serine proteases.

Asp and Glu are negatively charged at physiological pH. Because of their short side chain, the carboxyl group of Asp is rather rigid with respect to the main chain. This may be the reason why the carboxyl group in many catalytic sites is provided by Asp and not by Glu. Charged acids are generally found at the surface of a polypeptide.

In addition, Lys and Arg are found at the surface. They have long and flexible side chains presenting multiple rotamers of similar energies. In several cases, Lys and Arg take part in forming internal salt bridges or they help in catalysis. Because of their exposure at the surface of the polypeptide, Lys is a residue more frequently recognized by enzymes that either modify the side chain or cleave the peptide chain at the carbonyl end of Lys residues.

While the side group chemistry of an amino acid can guide the selection of a predetermined amino acid residue, the lack of a desired side group chemistry can be a criterion for excluding an amino acid residue for use as the predetermined amino acid. For example, sterically small and chemically neutral amino acids, such as alanine, can be excluded from Look-Through mutagenesis for lacking a desired chemistry.

3. Synthesizing Polypeptide Analog Libraries

In one embodiment, a library of polypeptide analogs is generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino acid. This differs from the oligonucleotides produced in saturation mutagenesis, random mutagenesis, or walk-through mutagenesis in that, for each oligonucleotide, only one mutation, as opposed to multiple mutations is made.

The oligonucleotides can be produced individually and then mixed or pooled as desired. When the codon of the wild type sequence and the codon for the predetermined amino acid are the same, no substitution is made.

Accordingly, the number of amino acid positions within the defined region will determine the maximum number of oligonucleotides made. For example, if five codon positions are altered with the predetermined amino acid, then five polynucleotides plus one polynucleotide representing the wild-type amino acid sequence are synthesized. Two or more regions can simultaneously be altered. In one embodiment, the amino acid residues (positions) within the defined region that are mutagenized are functional amino acid residues (positions). In another embodiment, the functional amino acid residues (positions) are exclusively mutagenized.

The mixture of oligonucleotides for generation of the library can be synthesized readily by known methods for DNA synthesis. The preferred method involves use of solid phase beta-cyanoethyl phosphoramidite chemistry. See U.S. Pat. No. 4,725,677. For convenience, an instrument for automated DNA synthesis can be used containing specified reagent vessels of nucleotides. The polynucleotides may also be synthesized to contain restriction sites or primer hybridization sites to facilitate the introduction or assembly of the polynucleotides representing, e.g., a defined region, into a larger gene context.

The synthesized polynucleotides can be inserted into a larger gene context of the polypeptide being mutagenized by using standard genetic engineering techniques. For example, the polynucleotides can be made to contain flanking recognition sites for restriction enzymes. See Crea, R., U.S. Pat. No. 4,888,286. The recognition sites are designed to correspond to recognition sites that either exist naturally or are introduced in the gene proximate to the DNA encoding the region. After conversion into double stranded form, the polynucleotides are ligated into the gene by standard techniques. By means of an appropriate vector (including, e.g., phage vectors, plasmids) the genes can be introduced into a cell-free extract, phage, prokaryotic cell, or eukaryotic cell suitable for expression of the mutant polypeptides.

In cases where the amino acid sequence of the polypeptide to be mutagenized is known or where the DNA sequence is known, gene synthesis is a possible approach. For example, partially overlapping polynucleotides, typically about 20-60 nucleotides in length can be designed. The internal polynucleotides are then phosphorylated annealed to their complementary partner to give a double-stranded DNA molecule with single-stranded extensions useful for further annealing. The annealed pairs can then be mixed together and ligated to form a full-length double-stranded molecule (see, e.g., FIG. 8). Convenient restriction sites can be designed near the ends of the synthetic gene for cloning into a suitable vector. The full-length molecules can be cleaved with those restriction enzymes and ligated into a suitable vector. Convenient restriction sites can also be incorporated into the sequence of the synthetic gene to facilitate introduction of mutagenic cassettes.

As an alternative to synthesizing polynucleotides representing the full-length double-stranded gene, polynucleotides which partially overlap at their 3' ends (i.e., with complementary 3' ends) can be assembled into a gapped structure and then filled in with a suitable polymerase to make a full length double-stranded gene. Typically, the overlapping polynucleotides are from 40-90 nucleotides in length. The extended polynucleotides are then ligated. Convenient restriction sites can be introduced at the ends and/or internally for cloning purposes. Following digestion with an appropriate restriction enzyme or enzymes, the gene fragment is ligated into a suitable vector. Alternatively, the gene fragment can be blunt end ligated into an appropriate vector.

In these approaches, if convenient restriction sites are available (naturally or engineered) following gene assembly, the degenerate polynucleotides can be introduced subsequently by cloning the cassette into an appropriate vector. Alternatively, the degenerate polynucleotides can be incorporated at the stage of gene assembly. For example, when both strands of the gene are fully chemically synthesized, overlapping and complementary degenerate polynucleotides can be produced. Complementary pairs will anneal with each other.

When partially overlapping polynucleotides are used in the gene assembly, a set of degenerate nucleotides can also be directly incorporated in place of one of the polynucleotides. The appropriate complementary strand is synthesized during the extension reaction from a partially complementary polynucleotide from the other strand by enzymatic extension with a polymerase. Incorporation of the degenerate polynucleotides at the stage of synthesis also simplifies cloning where more than one domain or defined region of a gene is mutagenized.

In another approach, the gene of interest is present on a single stranded plasmid. For example, the gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (Sayers, J. R. et al., Nucleic Acids Res. 16: 791-802 (1988)). This approach can circumvent multiple cloning steps where multiple domains are selected for mutagenesis.

Polymerase chain reaction (PCR) methodology can also be used to incorporate polynucleotides into a gene. For example, the polynucleotides themselves can be used as primers for extension. In this approach, polynucleotides encoding the mutagenic cassettes corresponding to the defined region (or portion thereof) are complementary to each other, at least in part, and can be extended to form a large gene cassette using a polymerase, e.g., using PCR amplification (see, e.g., FIG. 2).

The size of the library will vary depending upon the length and number of regions and amino acids within a region that are mutagenized. Preferably, the library will be designed to contain less than $10^{15}$, $10^{14}$, $10^{13}$, $10^{12}$, $10^{11}$, $10^{10}$, $10^9$, $10^8$, $10^7$, and more preferably, $10^6$ polypeptide analogs or less.

The description above has centered on the mutagenesis of polypeptides and libraries of polypeptides by altering the polynucleotide that encodes the corresponding polypeptide. It is understood, however, that the scope of the invention also encompasses methods of mutagenizing polypeptides by direct synthesis of the desired polypeptide analogs using protein chemistry. In carrying out this approach, the resultant polypeptides still incorporate the features of the invention except that the use of a polynucleotide intermediate is eliminated.

For the libraries described above, whether in the form of polynucleotides and/or corresponding polypeptides, it is understood that the libraries may be also attached to a solid support, such as a microchip, and preferably arrayed, using art recognized techniques.

4. Expression and Screening Systems

Libraries of polynucleotides generated by any of the above techniques or other suitable techniques can be expressed and screened to identify polypeptide analogs having desired structure and/or activity. Expression of the polypeptide analogs can be carried out using any suitable expression display system known in the art including, but not limited to, cell-free extract display systems (e.g., ribosome display and arrayed (e.g., microarrayed or macroarrayed) display systems), bacterial display systems, phage display systems, prokaryotic cells, and/or eukaryotic cells (e.g., yeast display systems).

In one embodiment, the polynucleotides are engineered to serve as templates that can be expressed in a cell free extract. Vectors and extracts as described, for example in U.S. Pat. Nos. 5,324,637; 5,492,817; 5,665,563, can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553).

Alternatively, the polynucleotides of the invention can be expressed in a convenient prokaryotic expression systems such as the bacterial *E. coli* expression system, such as that described by Pluckthun and Skerra. (Pluckthun, A. and Skerra, A., *Meth. Enzymol.* 178: 476-515 (1989); Skerra, A. et al., *Biotechnology* 9: 273-278 (1991)). The mutant proteins can be expressed for secretion in the medium and/or in the cytoplasm of the bacteria, as described by M. Better and A. Horwitz, *Meth. Enzymol.* 178: 476 (1989). In one embodiment, the single domains encoding VH and VL are each attached to the 3' end of a sequence encoding a signal sequence, such as the ompA, phoA or pelB signal sequence (Lei, S. P. et al., *J. Bacteriol.* 169: 4379 (1987)). These gene fusions are assembled in a dicistronic construct, so that they can be expressed from a single vector, and secreted into the periplasmic space of *E. coli* where they will refold and can be recovered in active form. (Skerra, A. et al., *Biotechnology* 9: 273-278 (1991)). For example, antibody heavy chain genes can be concurrently expressed with antibody light chain genes to produce antibody or antibody fragments.

In still another embodiment, the polynucleotides can be expressed in eukaryotic cells such as yeast using, for example, yeast display as described, e.g., in U.S. Pat. Nos. 6,423,538; 6,331,391; and 6,300,065. In this approach, the polypeptide analogs of the library are fused to a polypeptide that is expressed and displayed on the surface of the yeast. Other eukaryotic cells for expression of the polypeptides of the invention can also be used such as mammalian cells, for example myeloma cells, hybridoma cells, or Chinese hamster ovary (CHO) cells. Typically, the polypeptide analogs when expressed in mammalian cells are designed to be expressed into the culture medium, or expressed on the surface of such a cell. The antibody or antibody fragments can be produced, for example, as entire antibody molecules or as individual VH and VL fragments, Fab fragments, single domains, or as single chain antibodies (scFv) (see Huston, J. S. et al., *Proc. Natl. Acad. Sci. USA* 85: 5879-5883 (1988)).

The screening of the expressed polypeptide analogs (or polypeptides produced by direct synthesis) can be done by any appropriate means. For example, binding activity can be evaluated by standard immunoassay and/or affinity chromatography and catalytic activity can be ascertained by suitable assays for substrate conversion. Screening of the polypeptide analogs of the invention for proteolytic function can be accomplished using a standard hemoglobin plaque assay as described, for example, in U.S. Pat. No. 5,798,208.

5. Computer Modeling-Assisted Improved Look-Through Mutagenesis

The look-through mutagenesis of the invention may also be conducted with the benefit of structural or modeling information concerning the polypeptide analogs to be generated, such that the potential for generating analogs having the desired improved function is increased. The structural or modeling information can also be used to guide the selection of predetermined amino acid to introduce into the defined regions. Still further, actual results obtained with the polypeptide analogs of the invention can guide the selection (or exclusion) of subsequent polypeptides to be made and screened in an iterative manner. Accordingly, structural or modeling information can be used to generate initial subsets of polypeptide analogs for use in the invention, thereby further increasing the efficiency of generating improved polypeptides.

In a particular embodiment, in silico modeling is used to eliminate the production of any polypeptide analog predicted to have poor or undesired structure and/or function. In this way, the number of polypeptide analogs to be produced can be sharply reduced thereby increasing signal-to-noise in subsequent screening assays. In a particular embodiment, functional amino acid residues (positions) or hot spots are identified as suitable for mutagenesis whereas nonfunctional amino acid residues (positions) or cold spots, are excluded. In another particular embodiment, the in silico modeling is continually updated with additional modeling information, from any relevant source, e.g., from gene and protein sequence and three-dimensional databases and/or results from previously tested analogs, so that the in silico database becomes more precise in its predictive ability.

In yet another embodiment, the in silico database is provided with the assay results of previously tested polypeptide analogs and categorizes the analogs, based on the assay criterion or criteria, as responders or nonresponders, e.g., as polypeptide analogs that bind well or not so well or as being enzymatic/catalytic or not so enzymatic/catalytic. In this way, the mutagenesis of the invention can equate a range of functional response with particular structural information and use such information to guide the production of future polypeptide analogs to be tested. Accordingly, the method is especially suitable for screening antibody or antibody fragments for a particular function, such as binding affinity (e.g., specificity), stability (e.g., half life) and/or effector function (e.g., complement activation and ADCC) by targeting hot spots for mutagenesis. Accordingly, mutagenesis of noncontiguous residues within a region can be desirable if it is known, e.g., through in silico modeling, that certain residues in the region will not participate in the desired function. The coordinate structure and spatial interrelationship between the defined regions, e.g., the functional amino acid residues in the defined regions of the polypeptide, e.g., the predetermined amino acid(s) that have been introduced, can be considered and modeling. Such modeling criteria include, e.g., amino acid residue side group chemistry, atom distances, crystallography data, etc. Accordingly, the number of polypeptide analogs to be produced can be intelligently minimized.

In a preferred embodiment, one or more of the above steps are computer-assisted. The method is also amenable to be carried out, in part or in whole, by a device, e.g., a computer driven device. Accordingly, instructions for carrying out the method, in part or in whole, can be conferred to a medium suitable for use in an electronic device for carrying out the instructions. In sum, the methods of the invention are amendable to a high throughput approach comprising software (e.g., computer-readable instructions) and hardware (e.g., computers, robotics, and chips).

6. Exploring the Combinatorial Chemistry of Multiple Defined Regions

The present invention provides the important advantage of allowing for evaluation by mutagenesis of several different regions or domains of a polypeptide simultaneously. This can be done using the same or a different predetermined amino acid within each region, enabling the evaluation of amino acid substitutions in conformationally related regions, such as the regions that upon folding of the polypeptide, are associated to make up a functional site (e.g., the binding site of an antibody or the catalytic site of an enzyme). This, in turn, provides an efficient way to create new or improved functional sites.

For example, the six CDRs of an antibody that make up the unique aspects of the antigen binding site (Fv region), can be mutagenized simultaneously, or separately within the VH or VL chains, to study the three dimensional interrelationship of selected amino acids in this site. In one embodiment, the combinatorial chemistry of three or more defined regions are systematically explored using look-though mutagenesis, and preferably six defined regions, for example, the six CDRs of an antibody heavy and light chain variable region. For performing look-through mutagenesis on a CDR, typically 3, 4, 5, 6, 7, 8, 9, 10, 11, 12, 13, 14, 15, 16, 17, 18, 19, 20, 21, 22, 23, 24, 25, or more amino acid positions are altered. Functional amino acid resides are then distinguished from non-functional amino acid residues and identified as suitable for further mutagenesis.

Accordingly, the present invention opens up new possibilities for the design of many different types of novel and improved polypeptides. The method can be used to improve upon an existing structure or function of a protein For example, a binding site for an antibody or antibody fragment can be introduced or affinity for a pre-existing antigen, effector function and/or stability improved. Alternatively, the introduction of additional "catalytically important" amino acids into a catalytic domain of an enzyme can be performed resulting in a modified or enhanced catalytic activity toward a substrate. Alternatively, entirely new structures, specificities or activities may be introduced into a polypeptide. De novo synthesis of enzymatic activity can be achieved as well. The new structures can be built on the natural or consensus "scaffold" of an existing protein by mutating only relevant regions (e.g., functional amino acid residues (positions)) by the method of the invention.

7. Improved Look-Through Mutagenesis (LTM2) for Making New or Improved Antibodies The method of this invention is especially useful for modifying antibody molecules. As used herein, antibody molecules or antibodies refers to antibodies or portions thereof, such as full-length antibodies, Fv molecules, or other antibody fragments, individual chains or fragments thereof (e.g., a single chain of Fv), single chain antibodies (e.g., scFv), and chimeric antibodies. Alterations can be introduced into the variable region and/or into the framework (constant) region of an antibody. Modification of the variable region can produce antibodies with better antigen binding properties, and, if desired, catalytic properties. Modification of the framework region can also lead to the improvement of chemo-physical properties, such as solubility or stability (e.g., half life), which are especially useful, for example, in commercial production, bioavailabilty, effector function (e.g., complement activation and/or ADCC) and binding affinity (e.g., specificity) for the antigen. Typically, the mutagenesis targets the Fv region of the antibody molecule, i.e., the structure responsible for antigen-binding activity which is made up of variable regions of two chains, one from the heavy chain (VH) and one from the light chain (VL). In particular, the mutagenesis targets functional amino acid residues (positions) that have been determined to contribute to a measurable property of the antibody (e.g., antigen-binding, Fc receptor binding, etc.). Once the desired antigen-binding characteristics are identified, the variable region(s) can be engineered into an appropriate antibody class such as IgG, IgM, IgA, IgD, or IgE.

8. Improved Look-Through Mutagenesis (LTM2) for Making/Improving Catalytic/Enzymatic Polypeptides The method of the invention also is particularly suited to the design of catalytic proteins, particularly catalytic antibodies. Presently, catalytic antibodies can be prepared by an adaptation of standard somatic cell fusion techniques. In this process, an animal is immunized with an antigen that resembles the transition state of the desired substrate to induce production of an antibody that binds the transition state and catalyzes the reaction. Antibody-producing cells are harvested from the animal and fused with an immortalizing cell to produce hybrid cells. These cells are then screened for secretion of an antibody that catalyzes the reaction. This process is dependent upon the availability of analogues of the transition state of a substrate. The process may be limited because such analogues are likely to be difficult to identify or synthesize in most cases.

The method of the invention provides a different approach that eliminates the need for a transition state analogue. By the method of the invention, an antibody can be made catalytic by the introduction of suitable amino acids into the binding site of an immunoglobulin (Fv region). The antigen-binding site (Fv) region is made-up of six hypervariable (CDR) loops, three derived from the immunoglobulin heavy chain (H) and three from the light chain (L), which connect beta strands within each subunit. The amino acid residues of the CDR loops contribute almost entirely to the binding characteristics of each specific monoclonal antibody. For instance, catalytic triads (comprising of amino acid residues serine, histidine, and aspartic acid) modeled after serine proteases can be created in the hypervariable segments of the Fv region of an antibody with known affinity for the substrate molecule and screened for proteolytic activity of the substrate. In a preferred embodiment, functional amino acid residues (positions) that have been determined to contribute to a measurable property of the antibody, e.g., catalytic activity, are targeted.

In particular, the method of the invention can be used to produce many different enzymes or catalytic antibodies, including oxidoreductases, transferases, hydrolases, lyases, isomerases and ligases. Among these classes, of particular importance will be the production of improved proteases, carbohydrases, lipases, dioxygenases and peroxidases. These and other enzymes that can be prepared by the method of the invention have important commercial applications for enzymatic conversions in health care, cosmetics, foods, brewing, detergents, environment (e.g., wastewater treatment), agriculture, tanning, textiles, and other chemical processes. These include, but are not limited to, diagnostic and therapeutic applications, conversions of fats, carbohydrates and protein, degradation of organic pollutants and synthesis of chemicals. For example, therapeutically effective proteases with fibrinolytic activity, or activity against viral structures necessary for infectivity, such as viral coat proteins, can be engineered. Such proteases could be useful anti-thrombotic agents or anti-viral agents against viruses such as, for example, HIV, rhinoviruses, influenza, or hepatitis. In the case of oxygenases (e.g., dioxygenases), a class of enzymes requiring a co-factor for oxidation of aromatic rings and other double bonds, industrial applications in biopulping processes, conversion of biomass into fuels or other chemicals, conversion of waste water contaminants, bioprocessing of coal, and detoxification of hazardous organic compounds are possible applications of novel proteins. The identification of improvements to the foregoing is expedited by the methods of the invention by preferentially targeting functional amino acid residues (positions) that are more likely to contribute to the desired activity or property for which improvements are sought.

9. Combinatorial Mutagenesis Methods

In the combinatorial beneficial mutation approach, coding sequences are generated which represent combinations of the beneficial mutations identified by LTM. These combinations may be combinations of different beneficial mutations within a single CDR, mutations within two or more CDRs within a single antibody chain, or mutations within the CDRs of different antibody chains.

One combinatorial approach resembles the WTM method except that the selected codon substitutions within the CDRs are the different beneficial amino-acid substitutions identified by LTM. Thus, not every residue position in an antibody CDR will contain a mutation, and some positions will have multiple different amino acids substituted at that position. Overall, many if not all, combinations of beneficial mutations within a CDR or an antibody chain will be represented by at least one of the coding sequences in the library. As shown in Table 1, this coding-sequence library can be prepared by a modification of the WTM method, except that instead of placing codons for a single amino acid at each different position in the variable coding region, the codons that are introduced are those corresponding to all beneficial mutations detected in the LTM method. In order to keep the size of this library manageable, the mutations may be confined to one of the two heavy or light chains only.

In a second approach, individual gene fragments containing a single CDR region, and having a codon variation encoding all combinations of beneficial mutations within CDR reconstructed, e.g., by gene shuffling methods, to produce $V_L$ and $V_H$ chain coding sequences having combinations of beneficial mutations in all CDRs of a given chain or all CDRs in both chains.

A combinatorial library of mutations may also be generated by known gene shuffling methods, such as detailed in U.S. patent application 2003/005439A1, and U.S. Pat. No. 6,368,861, and (Stemmer WP (1994) *Proc Natl Acad Sci* 91(22): 10747-51), all of which are incorporated herein by reference. The method involves limited DNase I digestion of the collected mixed mutation clones to produce a set of random gene fragments of various pre-determined sizes (e.g. 50-250 base pairs). The fragments are then first denatured and the various separate fragments are then allowed to re-associate based on homologous complementary regions. In this manner, the re-natured fragments may incorporate differing mixed mutation CDRs in the re-assembled segments which are then extended by SOE-PCR as above, and a re-assembled chimera may then incorporate, at a minimum, at least two sets of beneficial CDR mixed mutations from each parental DNA source donor.

The present invention is further illustrated in the following examples, which should not be construed as limiting.

EXEMPLIFICATION

Throughout the examples, the following materials and methods were used unless otherwise stated.

Materials and Methods

In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g., Sambrook, Fritsch and Maniatis, *Molecular Cloning: Cold Spring Harbor Laboratory Press* (1989); *DNA Cloning*, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Antibody Engineering Protocols (Methods in Molecular Biology)*, 510, Paul, S., Humana Pr (1996); *Antibody Engineering: A Practical Approach (Practical Approach Series*, 169), McCafferty, Ed., Irl Pr (1996); *Antibodies: A Laboratory Manual*, Harlow et al., C. S. H. L. Press, Pub. (1999); *Current Protocols in Molecular Biology*, eds. Ausubel et al., John Wiley & Sons (1992); *Large-Scale Mammalian Cell Culture Technology*, Lubiniecki, A., Ed., Marcel Dekker, Pub., (1990). *Phage Display: A Laboratory Manual*, C. Barbas (Ed.), CSHL Press, (2001); *Antibody Phage Display*, P O'Brien (Ed.), Humana Press (2001); Border et al., Yeast surface display for screening combinatorial polypeptide libraries, *Nature Biotechnology*, 15(6): 553-7 (1997); Border et al., Yeast surface display for directed evolution of protein expression, affinity, and stability, *Methods Enzymol.*, 328: 430-44 (2000); ribosome display as described by Pluckthun et al. in U.S. Pat. No. 6,348,315, and Profusion™ as described by Szostak et al. in U.S. Pat. Nos. 6,258,558; 6,261,804; and 6,214,553.

Construction of the Test Gene

The ovalbumin wild type Fab sequences were used as templates for the $V_L$ and $V_H$ portions (SEQ ID NOS:1 and 2 respectively) for scfv construction using PCR and appropriate primers (SEQ ID NOS: 11 and 12) and $V_H$ oligonucleotides (SEQ ID NOS: 13-14). PCR reactions consisted of 2 μl each of 10 uM oligonucleotide stock, 0.5 μl Pfx DNA polymerase (2.5 U/μl), 5 μl Pfx buffer, 1 μl 10 mM dNTP, 1 μl 50 mM MgSO$_4$ and here conducted at 37.5 μl dH20 at 94 C for 2 min, followed by 24 cycles of 30 sec at 94 C, 30 sec at 50 C, and 1 min at 68 C followed by incubation at 68 C for 5 min. Oligonucleotides were synthesized on the 3900 Oligosynthesizer by Syngen Inc. (San Carlos, Calif.).

The above $V_L$ and $V_H$ PCR reactions were then separately extracted and purified (Qiagen PCR purification Kit as per manufacturer instructions) and an aliquot (1 μl) of each reaction was combined into a new tube. By means of the linker sequence at the 3' end of the $V_H$ reverse oligonucleotide (SEQ ID NOS: 14) and the 5' end of the $V_L$ forward oligonucleotide (SEQ ID NOS: 11), complementary binding allowed for single overlap extension PCR (SOE-PCR) assembly reaction to generate the full length ovalbumin scFv. The ovalbumin scFv PCR reaction was extracted and purified (Qiagen) for subsequent EcoR I and Not I endonuclease digestion (New England Biolabs as per manufacturer's directions). Full length ovalbumin scFv is subcloned into pYD1 vector and sequenced to confirm that no mutations, deletions or insertions were introduced (SEQ ID NO: 18) from the above PCRs. Once sequence verified, full length $V_H$ and $V_L$ ovalbumin serves as the wild type template for the subsequent strategies of building LTM libraries.

Additional PCR Conditions and Primer Design

Reaction conditions for T1 and T2 PCR are; 5 µl of 10 uM oligonucleotide mix, 0.5 µl Pfx DNA polymerase (2.5 U/µl), 5 µl Pfx buffer (Invitrogen), 1 µl 10 mM dNTP, 1 µl 50 mM MgSO4 and 37.5 µl dH20 at 94 C for 2 min, followed by 24 cycles of 30 sec at 94 C, 30 sec at 50 C, and 1 min at 68 C and then incubated for a 68 C for 5 min. The reactions are performed using a programmable thermocycler (MJ Research). T1 and T2 PCR reactions were gel purified (Qiagen) and equimolar aliquots from both were combined for SOE-PCR.

Figure 2:
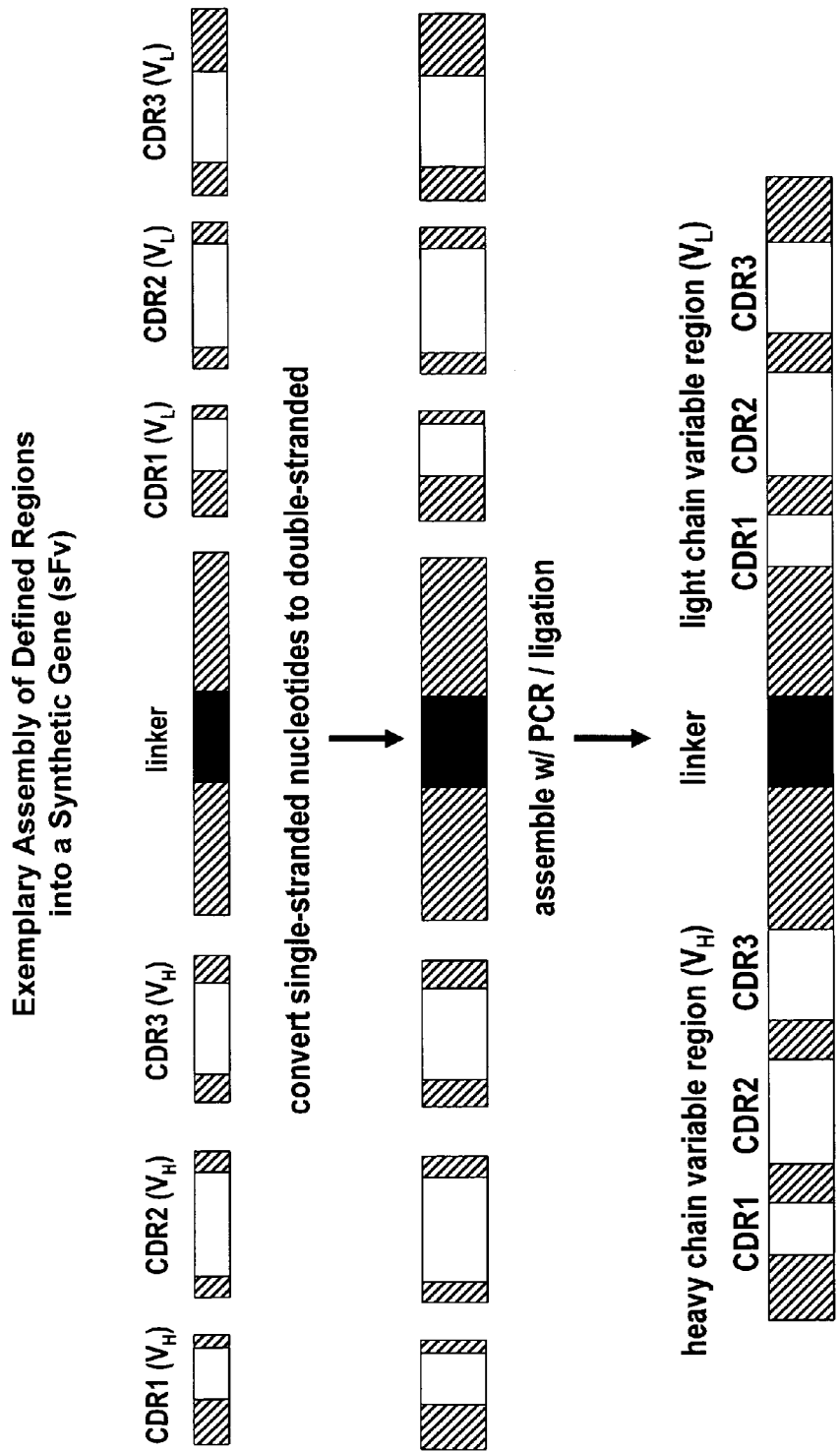
FIG. 2 illustrates a general approach for the use of polymerase chain reaction (PCR) to build defined regions of an antibody heavy and light chain for identifying functional amino acid residues, into a larger gene context.
Figure 4A:
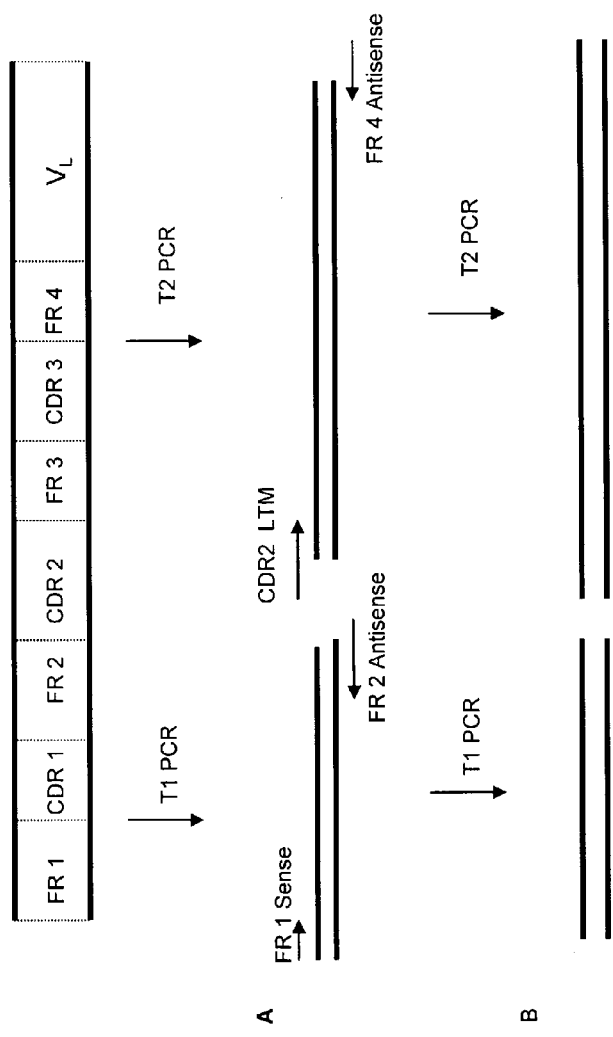
FIG. 4A discloses SEQ ID NO: 62.
Figure 4B:
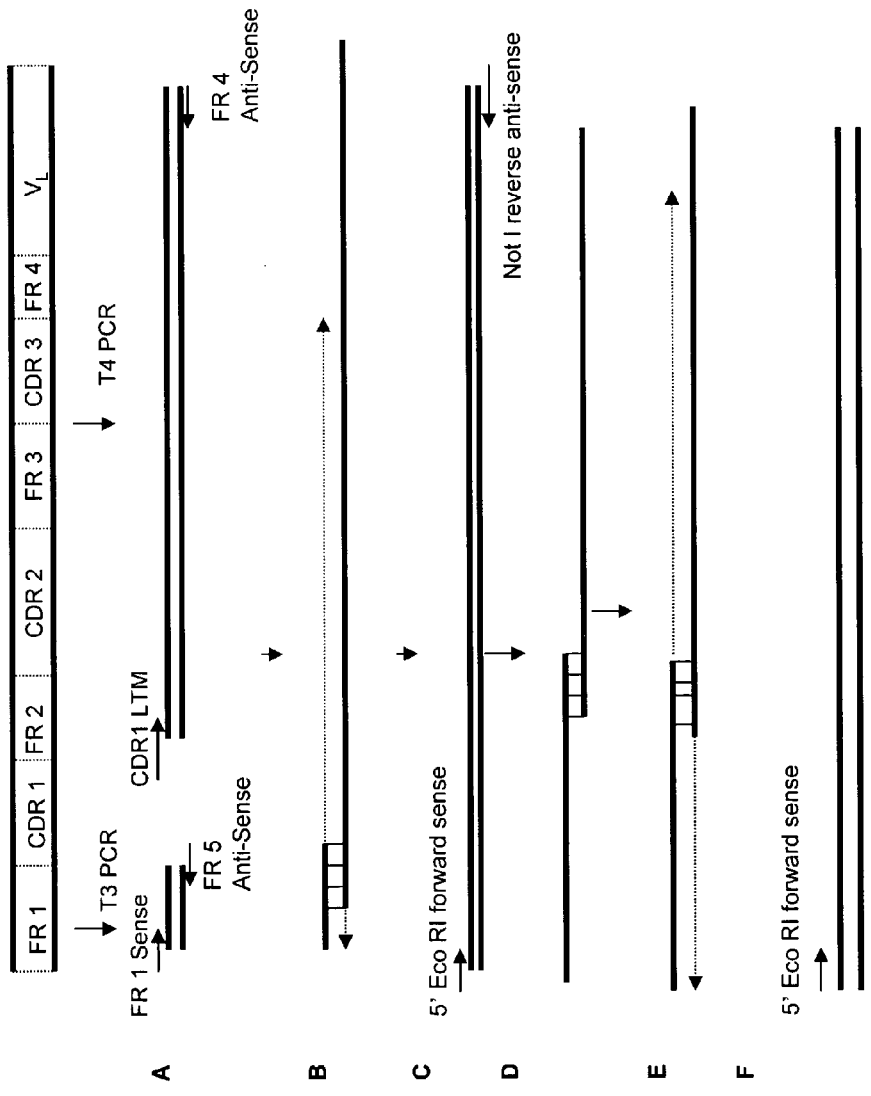
FIG. 4 illustrates the by single overlap extension polymerase chain reaction (SOE-PCR) for the production of an LTM $V_H$ CDR2 library; the production of multiple LTM $V_H$ CDR libraries; and an array of LTM library combinations containing both $V_H$ and $V_L$ CDRs.

SOE-PCR is a fast and simple method for combining DNA fragments that does not require restriction sites, restriction endonucleases, or DNA ligase. The T1 and T2 PCR products are designed to share end overlapping complementary sequences (FIG. 4) that would hybridize and allow PCR extension to produce a full length LTM ovalbumin scFv gene (FIGS. 2 and 4). The scFv PCR extension reaction used T1 and T2 aliquots (approximately 2 ul each) with 0.5 µl Pfx DNA polymerase (2.5 U/µl), 5 µl Pfx buffer (Invitrogen), 1 µl 10 mM dNTP, 1 µl 50 mM MgSO4 and 37.5 µl dH20 at 94 C for 2 min, followed by 20 cycles of 30 sec at 94 C, 30 sec at 50 C, and 1 min at 68 C and then incubated for a 68 C for 5 min.

A set of ovalbumin end specific 5' EcoR I sense (SEQ ID NO: 18) and ovalbumin 3' Not I antisense primers (SEQ ID NO: 19) were added to facilitate LTM ovalbumin amplification and incorporation of the restriction enzyme sites in the PCR amplicons (FIG. 4). The PCR extension reaction consisted of 4 µl of 10 uM oligonucleotide stock, 0.5 µl Pfx DNA polymerase (2.5 U/µl), 5 µl Pfx buffer (Invitrogen), 1 µl 10 mM dNTP, 1 µl 50 mM MgSO4 and 37.5 µl dH20 at 94 C for 2 min, followed by 24 cycles of 30 sec at 94 C, 30 sec at 50 C, and 1 min at 68 C and then incubated for a 68 C for 5 min.

PCR Product Cloning into a Yeast Cell Expression Vector pYD1

Figure 6:
FIG. 6 shows a schematic of a yeast expression vector for displaying proteins of interest, e.g., polypeptide analogs of the invention, on the surface of yeast for efficient identification of function (phenotype) and corresponding encoding sequence (genotype). 6×His tag disclosed as SEQ ID NO: 63.

The recipient plasmid pYD1 (FIG. 6) for anti-ovalbumin scFv expression, was prepared from an *E. coli* host by plasmid purification (Qiagen), digesting with the restriction enzymes, EcoRI and NotI, and terminally dephosphorylated with calf intestinal alkaline phosphatase. Ligation of the pYD1 vector and the above SOE-PCR products (digested by EcoRI and NotI), before subsequent *E. coli* (DH5α) transformation performed using standard techniques.

Yeast Cell Expression System

The pYD1 (FIG. 6) is an expression vector designed to display proteins of interest on the extracellular surface of *Saccharomyces cerevisiae*. By the sub-cloning the scFv gene into pYD1, scFvs becomes a fusion proteins with the AGA2 agglutinin receptor allowing cell surface secretion and display.

Transformation of Yeast Host Cells with pYD1 AGA2-scFv Constructs

Competent yeast host cells (500 µl) were prepared as per the manufacturer's instructions (Zymo Research Frozen-EZ Yeast Kit). Briefly, 500 µl of competent cells were mixed with 10-15 µg pYPD1 scFv library DNA after which 5 ml of EZ3 solution was added. The cell mixture was then incubated for 45 minutes at 30° C. with occasional mixing (three times). The transformed cells were centrifuged and resuspended in glucose selection media (Invitrogen).

Induction of AGA2-scFv

Cells were induced after growth in glucose selection media at 30° C. under shaking and aeration conditions for 48 hours until the $OD_{600}$=7 ($OD_{600}$=1 represents $10^7$ cells/ml). In particular, cells were collected and re-suspended in galactose selection/induction media (Invitrogen), until an $OD_{600}$=0.9 was reached after 48 hours at 20° C. Expression of the Aga2-scFv fusion protein from pYD1 was tightly regulated by the GAL1 promoter and depended on available galactose in the medium for GAL1 promoter induction.

Biotinylated Ovalbumin Preparation

Biotinylation of the target antigen ovalbumin was carried out according to the manufacturer's instructions (Molecular Probes FluoReporter Biotin-XX Labeling Kit (cat# F-2610)). Briefly, ovalbumin 300 µl of 1 mg/ml stock (Sigma), was added to 30 µl 1M Sodium Bicarbonate Buffer at pH 8.3 and 5.8 µl of Biotin-XX solution (20 mg/ml Biotin-XX solution in DMSO). The mixture was then incubated for 1 hour at 25° C. transferred to a micron filter tube, centrifuged, and the protein concentration was determined by light absorbance at $OD_{280}$.

FACS Monitoring of AGA2-scFv Expression and Ovalbumin Binding

To monitor induction and expression of the scFv construct, an aliquot of yeast cells ($8 \times 10^5$ cells in 40 µl) from the culture medium was collected by centrifugation for 5 minutes at 2300 rpm. The supernatant fluid was aspirated and then the cell pellet washed with 200 µl of ice cold PBS/BSA buffer (PBS/BSA 0.5% w/v). The cells were re-pelleted and supernatant removed before re-suspending in 100 µl of buffer containing the biotinylated ovalbumin (200 nM). The cells were left to bind the ovalbumin at 20° C. for 45 minutes after which they were washed twice with PBS/BSA buffer before the addition and incubation with streptavidin-FITC (2 mg/L) for 30 minutes on ice. Another round of washing in buffer was performed before final re-suspension in a volume of 400 µl in PBS/BSA. The cells were then analyzed on FACSscan (Becton Dickinson) using the CellQuest software package.

Example 1

Improved Look-Through Mutagenesis for the Development of High Affinity Antibodies In this example, the improved look-through mutagenesis of an exemplary scFv antibody, is described.

Briefly, improved look-through mutagenesis (LTM) was used to identify $V_H$ and $V_L$ CDR mutations in the $V_H$ and $V_L$ CDR regions of an antibody that enhance binding affinity to a chosen antigen, i.e., to identify the functional amino acid residues (positions) or hot spots that impart binding activity. The purpose of improved look-through mutagenesis (LTM2) is to introduce a selected substitution at targeted positions in a region of a polypeptide, e.g., the CDR regions of the variable antibody chain. Initially, coding libraries for both the $V_H$ and $V_L$ chains were constructed. Amino acid sequences of the reference anti-ovalbumin antibody $V_L$ and $V_H$ chains were identified (see SEQ ID NOS: 3-4) and a library of starting sequences for CDR1, CDR2, and CDR3 regions of the anti-ovalbumin VH chain identified by SEQ ID NOS: 5, 6 and 7, respectively, and those for CDR1, CDR2, and CDR3 regions of $V_L$ chain identified by SEQ ID NOS: 8, 9, and 10, were selected. Additionally, each $V_H$ or $V_L$ coding sequence library contains mutations for a selected representative functional amino acid in one, two, or all three CDRs in the selected chain.

Predetermined amino acids of $V_H$ CDR2 segment DINPSNGYTIYNQKFKG (SEQ ID NO: 9) (positions 56 to 69) from the ovalbumin wild type $V_H$ section SLEWIG-DINPSNGYTIYNQKFKG-FKGKATL (SEQ ID NO: 42), were selected for analysis. The polypeptide sequences SLEWIG (SEQ ID NO: 43) and KATLTVD (SEQ ID NO: 44) are portions of the $V_H$ frameworks 2 and 3 respectively flanking $V_H$ CDR2. In the design and synthesis of $V_H$ and $V_L$ CDR LTM oligonucleotides, the flanking framework sequence lengths of approximately 21 base pairs allow for complementary overlap and SOE-PCR. A reference oligonucleotide coding for the above CDR-H2 wild type sequence (in bold) (SEQ ID NO: 16) containing the flanking $V_H2$ and $V_H3$ portions (lowercase letters below) is shown below:

5'-agc ctt gag tgg att gga-GAT ATT AAT CCT AGC

AAT GGT TAT ACT ATC TAC AAC CAG AAG TTC AAG GGCttc aag ggc aag gcc aca ttg -3' (SEQ ID NO: 45)

Figure 3:
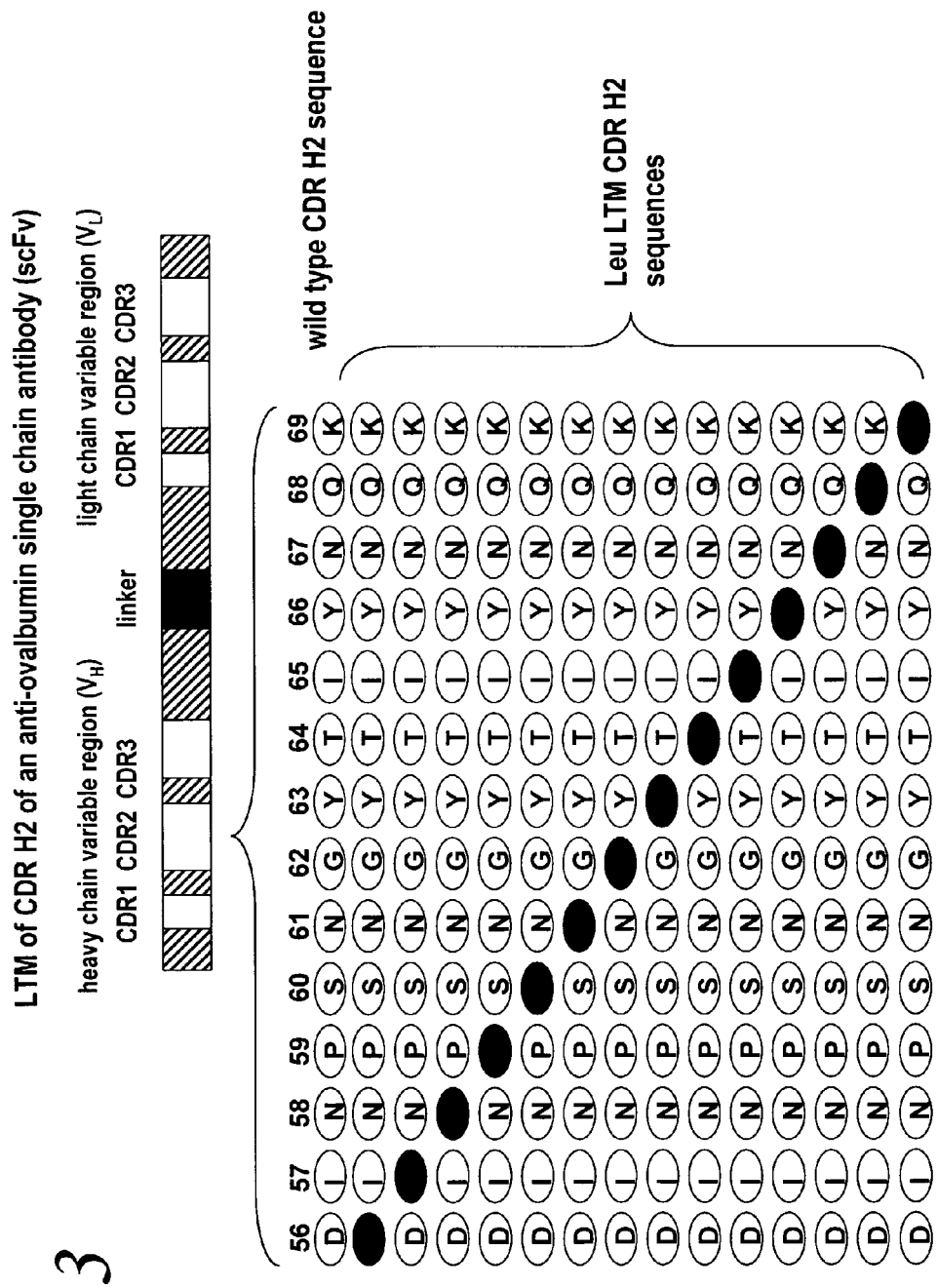
FIG. 3 illustrates the arrangement of variable light-chain ($V_L$) and variable heavy chain ($V_H$) CDRs in a synthetic single chain antibody (scFv) anti-ovalbumin gene context. In the application of LTM, a leucine amino acid is introduced into each of the fourteen residues 56-69 in $V_H$ CDR2 of the antibody (SEQ ID NOS 47-61, respectively, in order or appearance). For the application of LTM2, only those residues identified as functional are further explored by mutagenesis.

The leucine LTM of $V_H$ CDR2 involves serially substituting only one leucine at a time, in every or at a plurality of CDR2 positions. FIG. 3 illustrates LTM application for introducing a leucine amino acid into each of the fourteen residues (positions 56-69) in the $V_H$ CDR2 region of anti-ovalbumin scFv. In performing leucine LTM, fourteen separate oligonucleotides encoding all possible $V_H$ CDR2 leucine positional variants were synthesized (SEQ ID NOS:17-33) with each having only one leucine replacement codon (in bold) bordered by anti-ovalbumin wild type sequence. A total of fourteen different peptides are then generated, and no "undesired" or multiple-substitution sequences are produced.

In an alternative to introducing leucine to a "plurality of positions", one may choose not to include one or more of the above CDR2 LTM oligonucleotides. Hence, for example, the LTM oligonucleotides (SEQ ID NOS: 20 and 21) for positions 59 and 60 respectively can be excluded and thus improved look-through mutagenesis (LTM2) would only be performed on positions 56-58 and 61 to 69. Based on the different combinations of using a "plurality of positions", permutations of LTM2 can be performed without necessarily restricting to each and every position within a CDR.

The approach in making the LTM CDR2 library is summarized in FIGS. 2 and 4. Separate PCR reactions, T1 and T2, are carried out using primer pairs FR1 sense (SEQ ID NO: 34) and FR2 antisense (SEQ ID NO: 35) and the above pooled CDR-2 LTM leucine oligonucleotides (SEQ ID NO: 18-33) with FR4 anti-sense primer (SEQ ID NO: 36) respectively. Primer FR1 sense contains sequences from the 5' terminus of the ovalbumin gene and FR2 anti-sense contains the antisense sequence from the 3' terminus of ovalbumin framework 2 so that the ovalbumin CDR1, framework regions 1 and 2 was amplified in the T1 PCR reaction (FIGS. 2A and 2B). The primer FR4 AS contains anti-sense sequence from the 3' terminus of the ovalbumin gene, CDR2 LTM oligonucleotides contain sequences from the 5' terminus of the ovalbumin CDR2 region with the incorporated CDR2 LTM codon mutations to amplify the remaining portion of ovalbumin (fragment CDR2, FR3, CDR3, FR4 and the entire $V_L$ segment) while concurrently incorporating the mutagenic codon(s).

Double and Triple CDR mutations (in different combinations of CDR1, 2, and 3) were created as above but instead of using the wild type ovalbumin gene as a PCR template, a previously generated LTM ovalbumin library was selected. For example, to create $V_H$ chains in which both CDR1 and CDR2 are mutated with wild-type CDR3 and $V_L$ segments, the previously constructed LTM CDR2 mutant genes were used as templates and then SOE-PCR was conducted to incorporate the CDR1 oligonucleotides to generate the Double LTM mutations (summarized in FIGS. 2 and 4).

In this example, the T3 PCR reaction used primer pairs FR1 sense (SEQ ID NO: 34) and FR5 antisense (SEQ ID NO: 37) to amplify the framework region 1 (FR 1). The T4 PCR reaction used the pooled CDR1 LTM histidine oligonucleotides (SEQ ID NOS: 38-41) with FR4 anti-sense primer (SEQ ID NO: 36) to amplify the remaining FR2, CDR2 LTM, FR3, CDR3, FR4 and $V_L$ portions of ovalbumin (FIG. 4). T3 and T4 PCR reactions were then purified and equimolar aliquots from both were combined for SOE-PCR (FIG. 4) to produce an ovalbumin scFv His CDR1 and Leu CDR2 double LTM library. A set of ovalbumin end specific 5' Eco RI sense (SEQ ID NO: 13) and ovalbumin 3' NotI antisense primers (SEQ ID NO: 12) were then added to facilitate LTM ovalbumin amplification and cloning into the pYPD1 expression vector.

The His CDR1 and Leu CDR2 double LTM library was then used as templates to further incorporate LTM CDR3 oligonucleotides to make the Triple CDR LTM libraries. By progressively utilizing the starting single and double LTM libraries, a more complex array of LTM library combinations in both the $V_H$ and $V_L$ CDR was developed. For example, once the $V_H$ Triple LTM CDR1, CDR2, and CDR3 library was constructed, designated as the 111 library template in the top row of FIG. 5, introduction of LTM $V_L$ CDR1 into the $V_H$ 111 templates produces a library of 4 LTM CDRs (FIG. 5).

Figure 7:
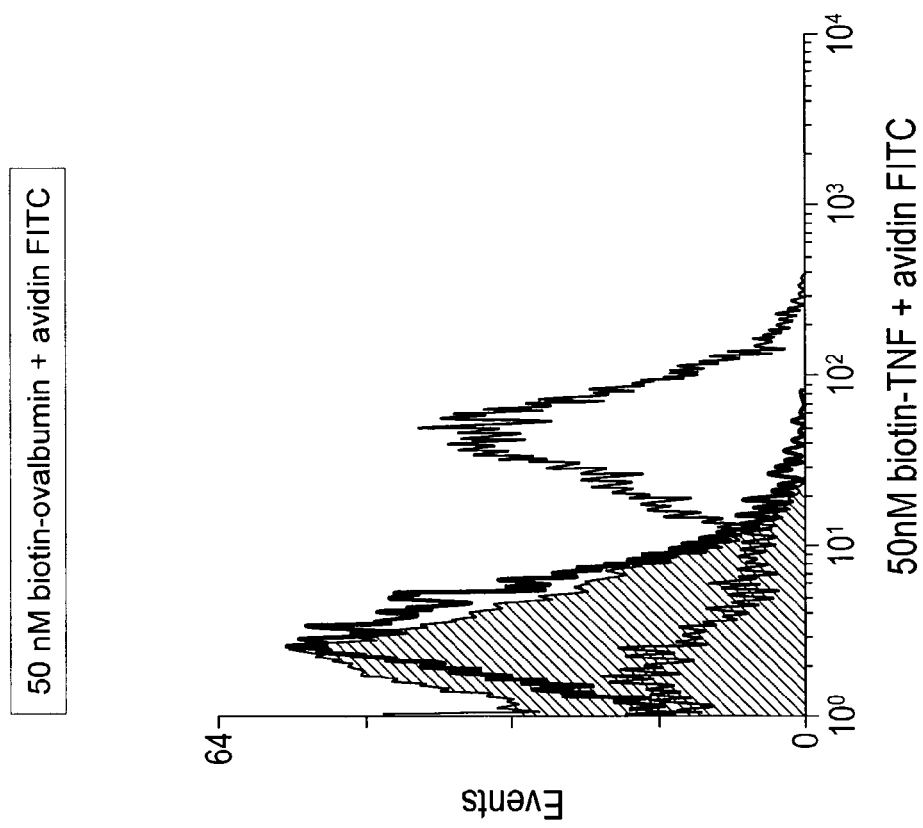
FIG. 7 represents a Fluorescence-Activated Cell Sorter (FACS™) plot of the binding of biotinylated ovalbumin and streptavidin FITC to wild type anti-ovalbumin scFv (gray line); pYD1 vector alone (solid gray area); and control scFv (black line).

The FACS plot shown in FIG. 7 illustrates that ovalbumin scFv binding molecules were generated in the construction of the foregoing library. In particular, molecules of biotinylated ovalbumin and streptavidin FITC (the "green" line) produced a peak signal response a magnitude higher compared to signal from the empty vector pYD1 with biotinylated ovalbumin and streptavidin FITC (dark shaded area).

Example 2

High Throughput Library Screening for the Development of Antibodies with Enhanced Properties In this example, the high throughput screening of exemplary single chain antibodies with enhanced properties, is described.

Figure 9:
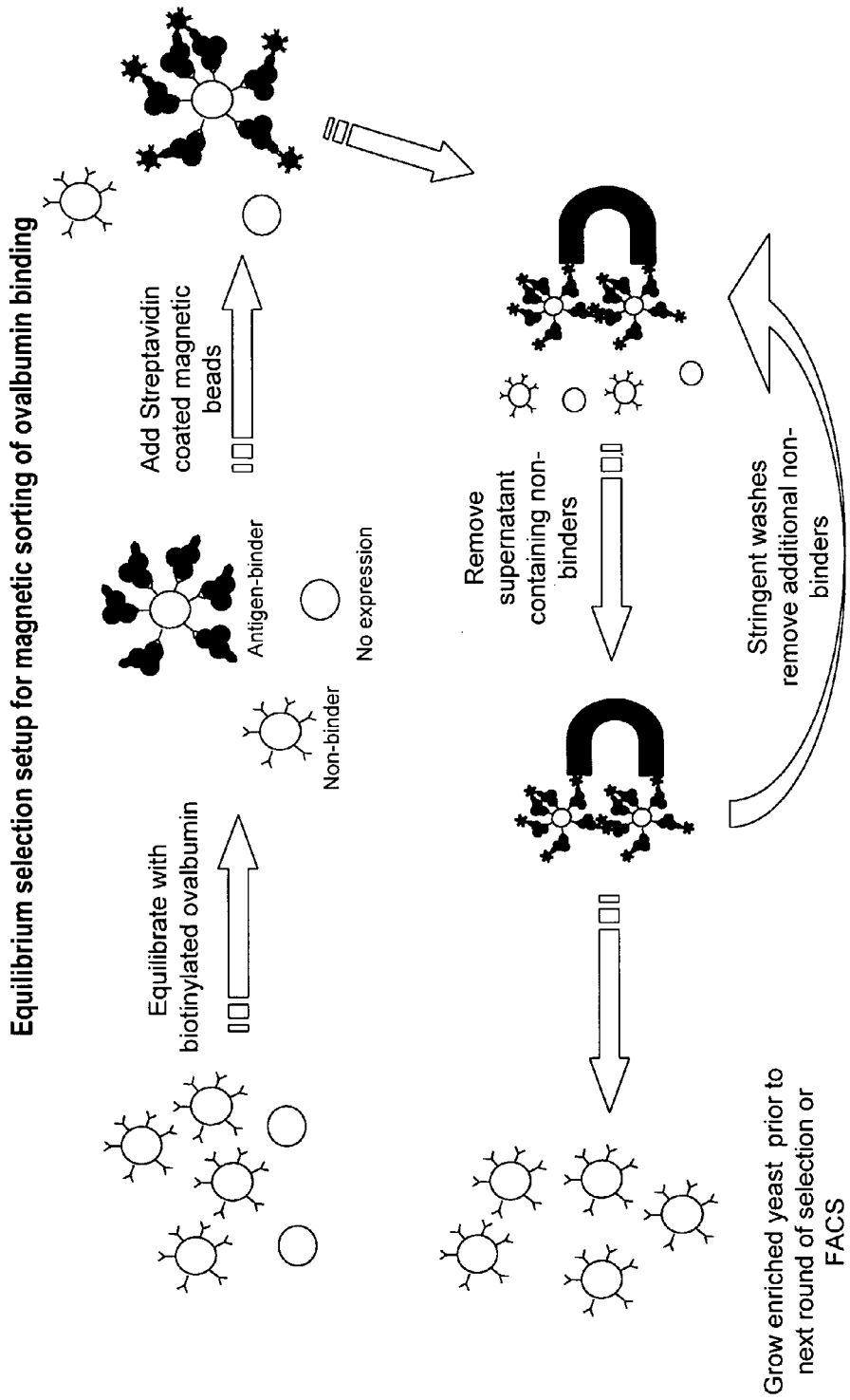
FIG. 9 illustrates steps in the screening of scFv antibodies (e.g., anti-ovalbumin) formed in accordance with the present invention for improved binding affinity based on equilibrium binding kinetics (e.g., to ovalbumin).

FIG. 9 depicts a generalized scheme for enriching the ovalbumin specific high affinity binding clones from the heterogeneous LTM2 scFv library. After induction in galactose media, the yeast cell library ($10^7$) was resuspended in PBS/BSA buffer (total volume of 500 µl). Biotinylated ovalbumin was added to the yeast suspension for a final concentration 50 nM and incubated at 25° C. for 2-3 hours with shaking. The yeast cells were pelleted, washed 3 times, and resuspended in 300 µl ice cold PBS/BSA buffer of buffer with $1 \times 10^8$ streptavidin coated magnetic beads added. The bead cell mixture was incubated on ice for 2 minutes with gentle mixing by inversion to form a binding complex consisting of yeast high-affinity scFv expressing cells, biotinylated ovalbumin, and streptavidin coated magnetic beads. The column (tubes) containing bound complexes were then applied to the magnetic column holder for 2 minutes after which the supernatant was removed by aspiration. The column was removed from the magnet holder, and 300 µl ice cold PBS/BSA was added to re-suspend the bound. The bound complexes were washed again in order to remove those scFv clones of low-affinity and other non-specifically bound cells.

The column was then removed from the magnetic holder whereupon 1 ml of glucose selection media was added to the recovered yeast cells for a 4 hour incubation at 30° C. The magnet holder was then re-applied to the culture tube to remove any remaining magnetic beads. The yeast culture was then grown in glucose selection media at 30° C. for 48 hours before scFv induction in galactose selection media. In the second selection round, the ovalbumin concentration was then lowered from 10 nM to 0.5 nM. the ovalbumin binding, complex formation, and yeast cell enrichment and re-growth were performed as described above. For the final third selection round, the ovalbumin concentration was further reduced to 0.1 nM.

Figure 8:
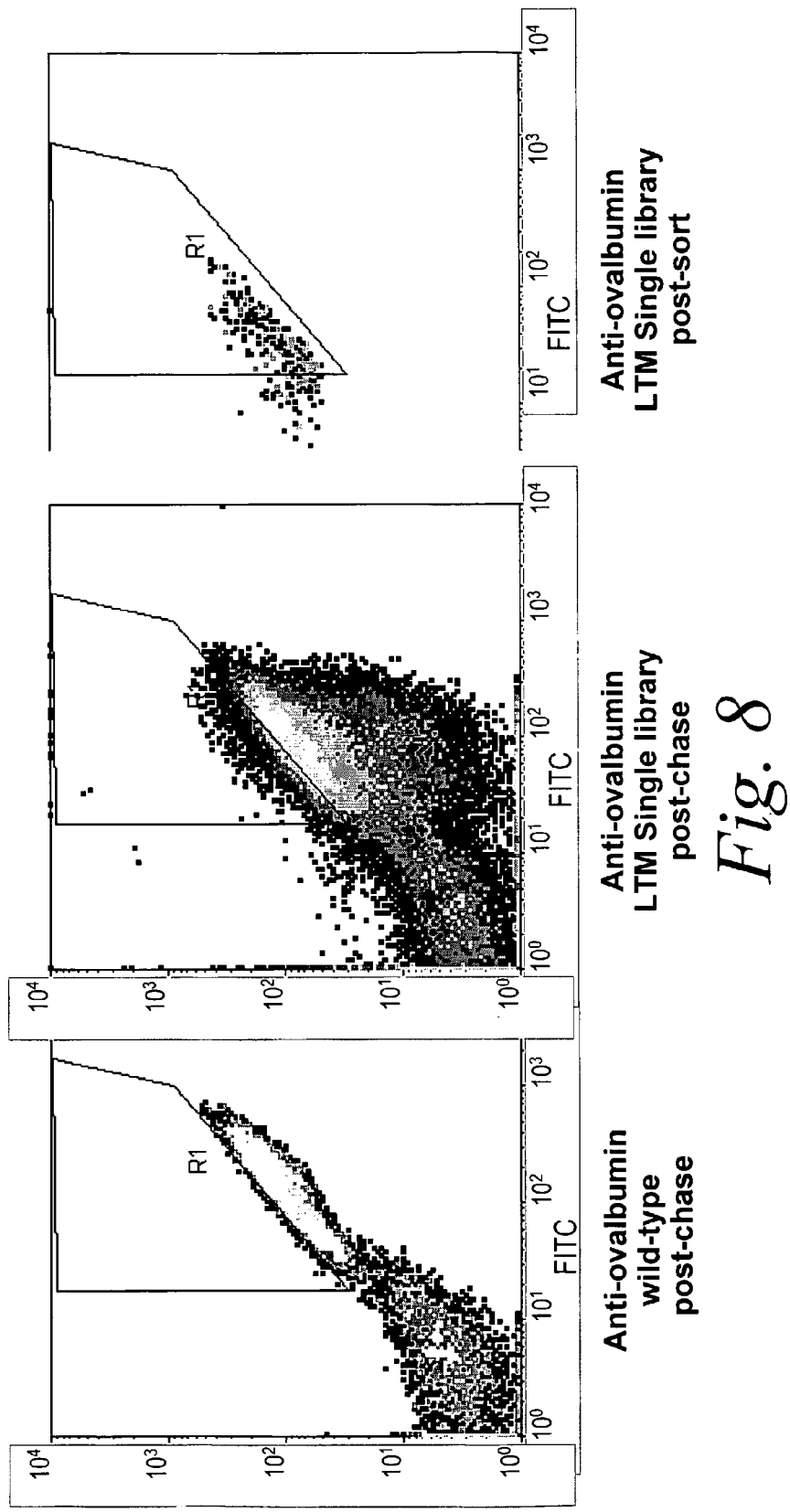
FIG. 8 represents Fluorescence-Activated Cell Sorter (FACS™) plots showing a selection gate (the R1 trapezoid) for identifying only those LTM clones that expressed the scFv fusion with a higher binding affinity to ovalbumin than the anti-ovalbumin wild type antibody (left panel), the distribution of binding affinities of the total LTM library (center panel), and a post sort FACS analysis (right panel) to confirm that >80% of the pre-screen anti-ovalbumin scFv clones were within the predetermined criteria.
Figure 10:
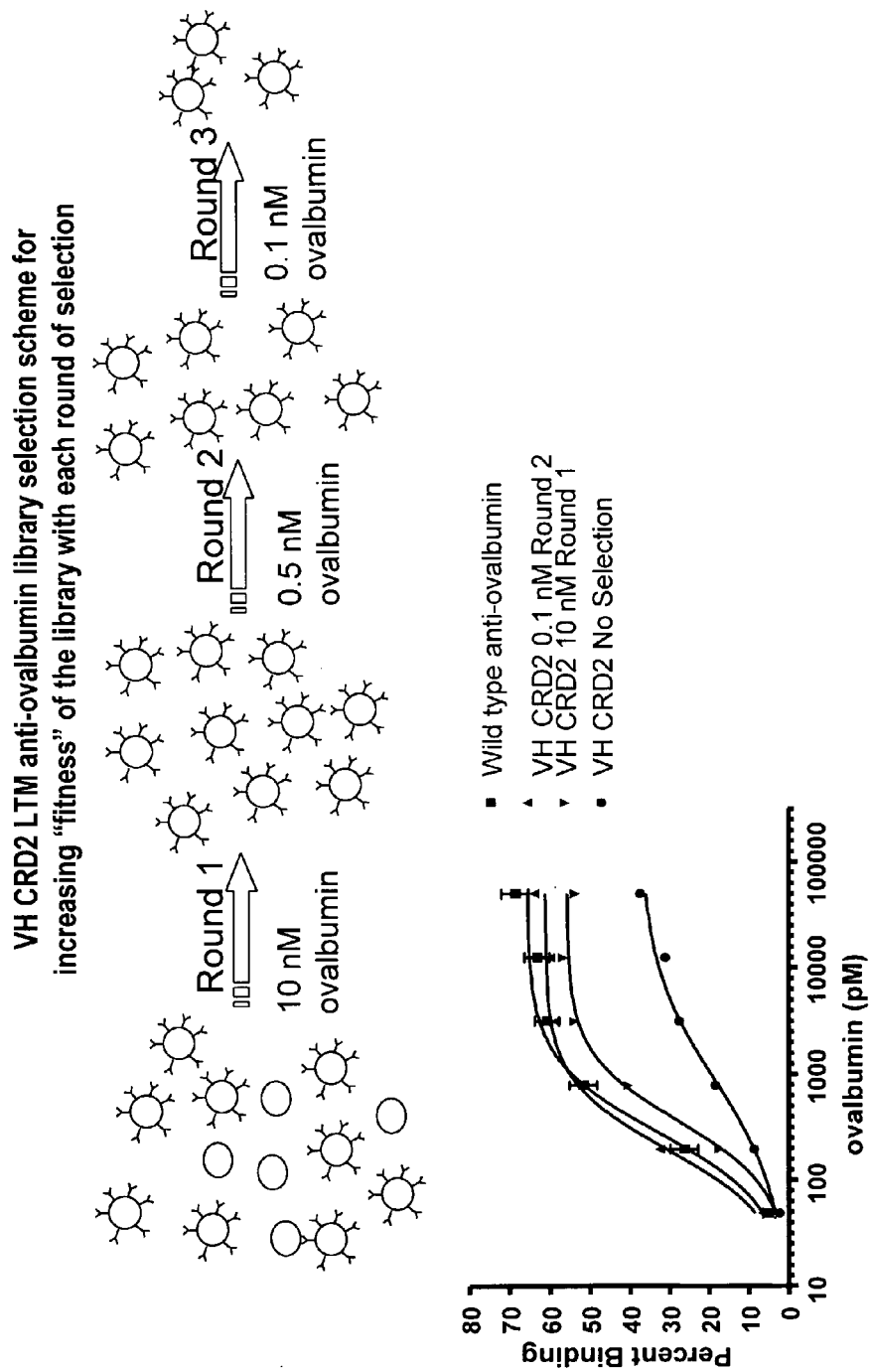
FIG. 10 shows equilibrium binding curves for anti-ovalbumin scFv expressing cells prior to selection (circles), after one round of selection (light triangles), after two rounds of selection (dark triangles), and for the anti-ovalbumin wild-type reference antibody (black squares).

Ovalbumin $EC_{50}$ binding, or "fitness" from each of the above rounds of progressive enrichment was evaluated by FACS (see FIG. 8). Results shown in FIG. 8 illustrates that the initially transformed $V_H$ LTM CDR2 yeast library, with no prior selection (closed circles), as well as the overall fitness in terms of percent binders (y-axis). Clones expressing functional anti-ovalbumin scFvs and their affinity, as measured by the ovalbumin $EC_{50}$ (x-axis), were inferior compared to the anti-ovalbumin wildtype antibody. However, after one round of selection (10 nM), the "fitness" curve (light triangles) improved in percent binders and the $EC_{50}$ for ovalbumin binding was in the same nM range as the ovalbumin wild type. After the second selection round (0.1 nM), the enriched population (dark triangles) exhibited an overall "fitness" that approached that of the ovalbumin wild type (solid squares) (FIG. 10). The recovered yeast cells from the second round of enrichment were then plated onto solid media in order to isolate single clones for individual binding analysis and sequence determination.

In an alternative methodology, the LTM2 yeast cell libraries were enriched for high affinity anti-ovalbumin scFv clones by FACS. Library construction, transformation, liquid media propagation and induction, were carried out as above. After scFv induction, the cells were incubated with biotinylated ovalbumin at saturating concentrations (400 nM) for 3 hours at 25° C. After washing the cells, a 40 hour cold chase using unlabelled ovalbumin (1 uM) at 25° C. was performed. The cells were then washed twice with PBS/BSA buffer, labeled with Streptavidin PE (2 mg/ml) anti-HIS-FITC (25 nM) for 30 minutes on ice, washed and re-suspended as described above for FACS analysis.

Wild type anti-ovalbumin was initially FACS analyzed to provide a reference signal pattern for FACS sorting of the yeast LTM library (FIG. 8, left panel). From the ovalbumin FACS plot, a selection gate (the R1 trapezoid) was drawn to obtain only those clones that expressed the scFv fusion (as detected by anti-HIS-FITC) and concomitantly would display a higher binding affinity to ovalbumin (a stronger PE signal) compared to wild type anti-ovalbumin. FIG. 8 (middle panel) demonstrates that approximately 5% of the total LTM library screened was selected by the R1 gate. After FACS collection of these high anti-ovalbumin scFv clones, a post-sort FACS analysis (FIG. 8, right panel) was performed to confirm that >80% of the pre-screen anti-ovalbumin scFv clones were within the predetermined criteria. The FACS sorted scFv clones were then grown in glucose selection media at 30° C. for 48 hours and plated on solid media to isolate individual clones. Clones were then grown in glucose selection media, re-induced in galactose selection media, and analyzed for their $EC_{50}$ and/or $k_{off}$ characteristics.

Example 3

High Throughput Library Screening for the Development of Antibodies with Improved $K_{off}$ Rates In this example, the high throughput screening of exemplary single chain antibodies with enhanced $K_{off}$ rates, is described.

Briefly, pre-sorted clones from the above example were grown overnight in glucose selection media and then plated on solid media to isolate single colonies. From single colonies, liquid cultures of clones were grown in glucose selection media at 30° C. with shaking for 48 hours before pelleting and re-suspending in galactose selection media for the appropriate OD time period. Because the FACS pre-sort enriches (by approximately 80%) but does not eliminate all undesirable clones, the $EC_{50}$ of the isolated clones was characterized to eliminate those that display binding values inferior to anti-ovalbumin wild type reference antibody (as detailed above). Only those isolates with comparable or superior $EC_{50}$ values were then selected for further $K_{off}$ analysis.

Figure 11:
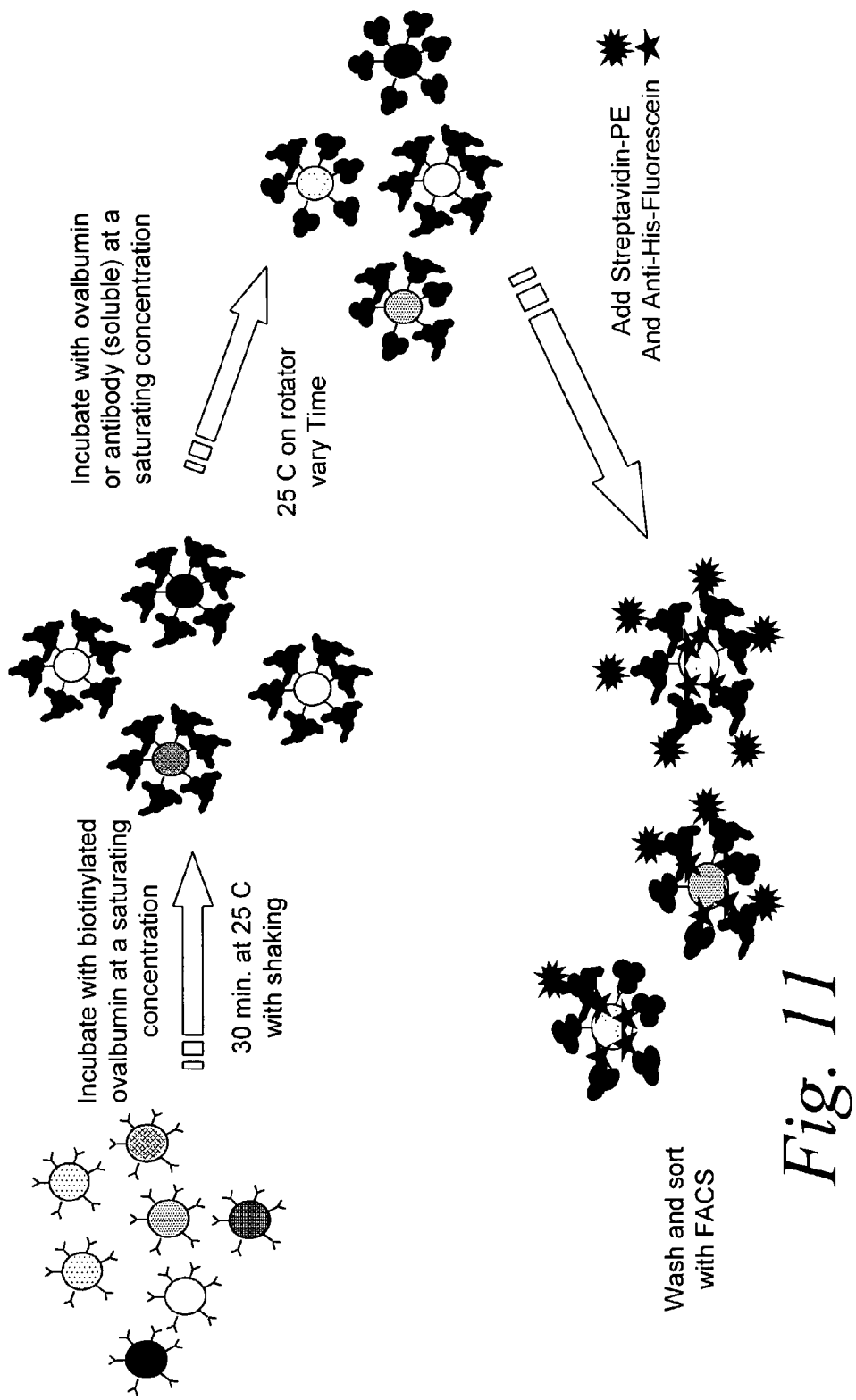
FIG. 11 illustrates typical steps for screening of antibodies formed in accordance with the present invention for high binding affinity based on particular binding kinetics, e.g., antibody $K_{off}$ constants, using the test antigen ovalbumin.

A scheme for analyzing the kinetics of candidate molecules is shown in FIG. 11. Specifically, yeast cells (approximately $5\times10^6$) after induction in galactose selection media, were pelleted and re-suspended in PBS/BSA buffer (1 ml). Biotinylated ovalbumin (400 nM final concentration) was then added to the re-suspended cells and allowed to incubate or 2 hours at 25° C. with continuous gentle mixing. The biotinylated-ovalbumin and yeast cell complex was then washed and re-suspended in PBS/BSA buffer and unlabelled ovalbumin was then added (to a final concentration of 1 µM) to the yeast cell mixture which was further incubated for 24 hours at 25° C. Timed sample aliquots were then taken every two hours for the next 24 hours. The cell mixtures were then washed and re-suspended in chilled PBS/BSA buffer and staining antibody α-SA PE (2 µg/ml). After incubation for 30 minutes on ice with periodic mixing, the cell mixture was then twice washed and analyzed by FACS as above.

Figure 12:
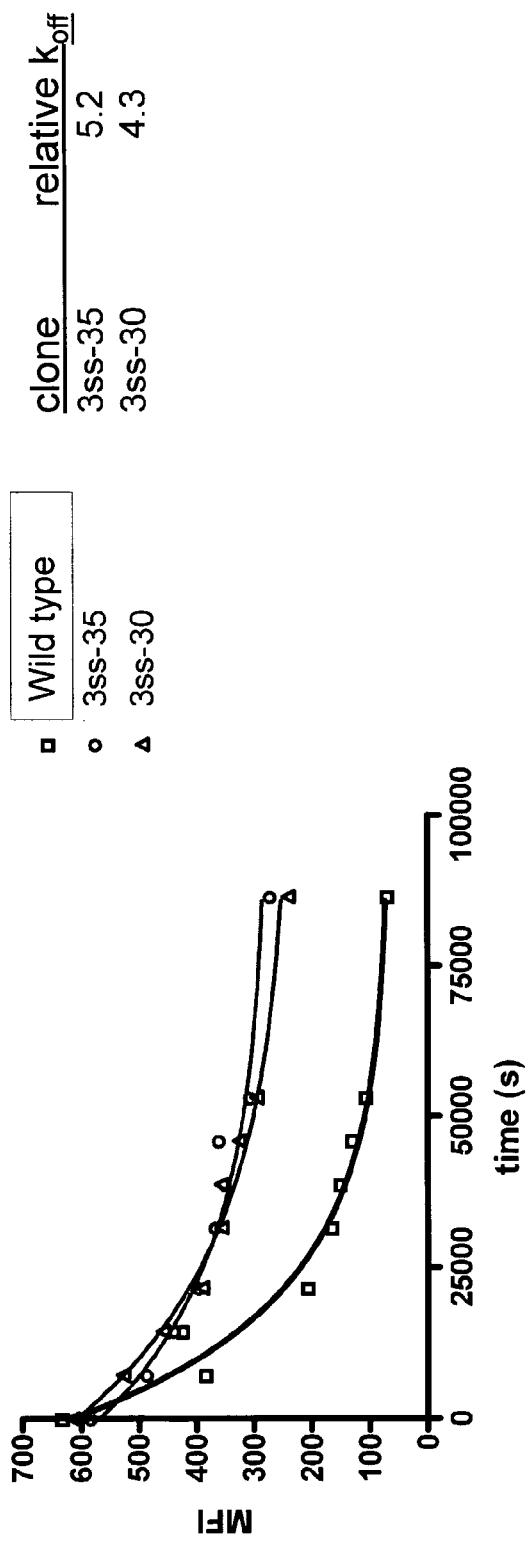
FIG. 12 shows the identification of enhanced properties in two clones (i.e., higher relative $K_{off}$ as compared to an reference antibody (square)) using the methods of the invention.

Results from the $K_{off}$ assays (FIG. 12) demonstrated two clones (i.e., 3ss-35; 3ss-30) as having a higher relative $K_{off}$ as compared to the wild type anti-ovalbumin antibody. In other words, when exchanging the bound biotinylated ovalbumin for the unlabelled ovalbumin during the 24 hour sampling period, 3ss-35 and 3ss-30 released the previously bound biotinylated ovalbumin at a much slower rate (circles and triangles respectively in FIG. 12) compared to anti-ovalbumin wild type, (squares FIG. 12) which exhibited a much sharper decrease in MFI (mean fluorescence intensity) over the first 8 hours.

Example 4

High Throughput Library Screening for the Development of Antibodies with Improved $EC_{50}$ Binding In this example, the high throughput screening of exemplary single chain antibodies with enhanced EC50 binding activity is described.

Briefly, a pre-determined amount of yeast cells ($8\times10^5$ cells in 40 µl) anti-ovalbumin scFvs (wild type and LTM library) was incubated with 1:4 serial dilutions of biotinylated ovalbumin (200 nM, 50 nM, 12.5 nM, 3.1 nM, 0.78 nM, and 0.19 nM final concentrations in a total volume of 80 µl) at 20° C. for 45 minutes followed by 5-10 minutes on ice. The yeast cells were then washed and re-suspended in 5 ml of PBS/BSA buffer after which streptavidin-PE (2 mg/ml) and αHIS-FITC (25 nM) was added to label the cells during a 30 minute incubation on ice. Another round of washing was performed before re-suspending in 400 µl of PBS/BSA buffer and analysis on FACSscan using CellQuest software.

Figure 13:
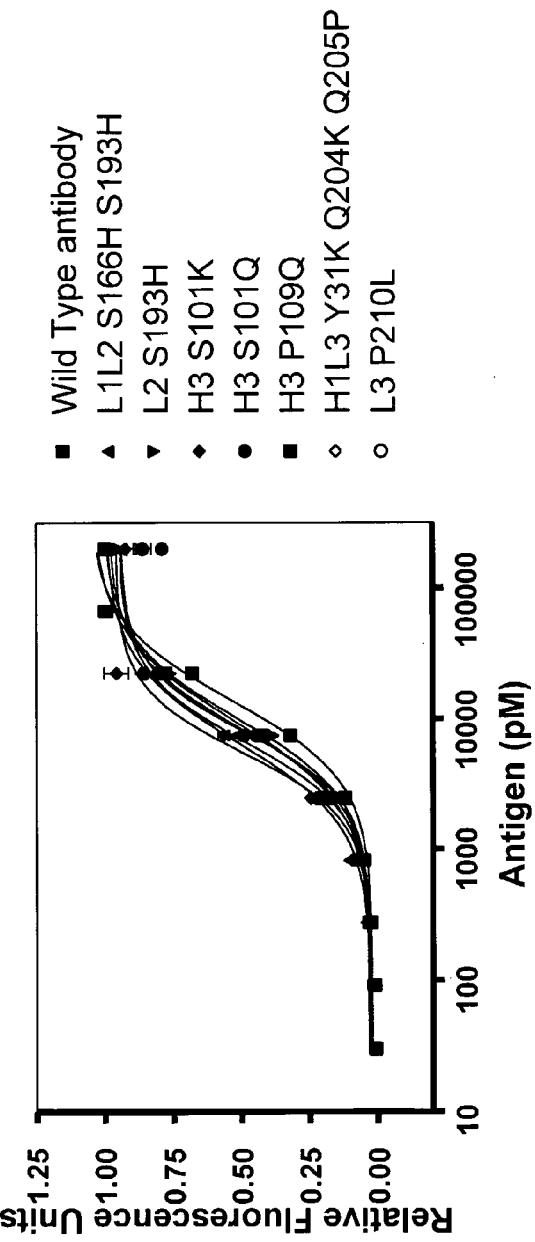
FIG. 13 represents the enhanced properties (see fold better than wild type) of a subset of improved clones having lower $EC_{50}$ values with respect to an anti-ovalbumin wild-type reference antibody control (square).

FIG. 13 exemplifies a subset of improved clones, relative to anti-ovalbumin, having lower $EC_{50}$ values (the binding curves have shifted to the left with respect to the wild type). These relative $EC_{50}$ values as compared to anti-ovalbumin wild type and the relative fold increase are shown. For example, the clone H3 S101Q exhibited a 2.1 fold improvement in ovalbumin binding. Nomenclature identification of this clone H3 S101Q, indicates that it was from a $V_H$ CDR3 glutamine LTM single library.

The resulting enhanced-binding affinity antibodies produced provide a map of beneficial amino acid mutations in the $V_H$ and $V_L$ CDRs of the anti-ovalbumin antibody that were associated with enhanced binding activity. Putative individual amino acid $V_H$ and $V_L$ CDR mutations associated with the enhanced-affinity scFv antibodies are shown in FIG. 13. Mutations were found in each $V_H$ and $V_L$ CDR and single-, double-, and triple-CDR mutations, and include each of the nine different amino acids tested. FIG. 13 exemplifies that four independent $V_H$ CDR-H3 H3 G102K clones identified from the above $EC_{50}$ and/or kinetics ($K_{off}$) screen, can be recovered. The double LTM $V_L$ L1L2 S166H S193H mutant from the $EC_{50}$ screen (FIG. 14) also illustrates that enhanced ovalbumin binding occurs when there is a synergistic interaction between these two CDR1 S166H and CDR2 S193H substitutions.

Results also indicate that (see FIG. 14) unique sequences for scFv anti-ovalbumin antibodies selected in accordance with the above $EC_{50}$ and/or Koff method using coding sequences containing single mutations at one, two or at all three CDRs in either the $V_H$ or $V_L$ chains, can be obtained. Some of the amino acid substitutions were found to be recovered in a higher preponderance in certain CDRs. For example in $V_H$ CDR1, there were seven independent single Lys substitutions in the positions of D30K, Y31K, M33K and W35K. The high preponderance of Lys in CDR1 indicates that enhanced ovalbumin binding occurs when there is a net increase of positive charges contributed by CDR1 during antigen contact. Examination of the recovered amino acid substitutions also revealed that a favored substitution occurs for $V_H$ CDR2 and CDR3. For example, it was observed that multiple scattered Lys replacements occur in CDR2 while CDR3 displays concentrated G102K and G104K replacements. Results also reveal that additionally, there were multiple Gln replacements, another polar amino acid, in CDR3 at positions 107, 108, 109, and 111. These results indicate that there is a unique "chemical motif" of corresponding negative and/or hydrophilic charges on ovalbumin that is contacted by these replaced CDR residues.

Figure 14:
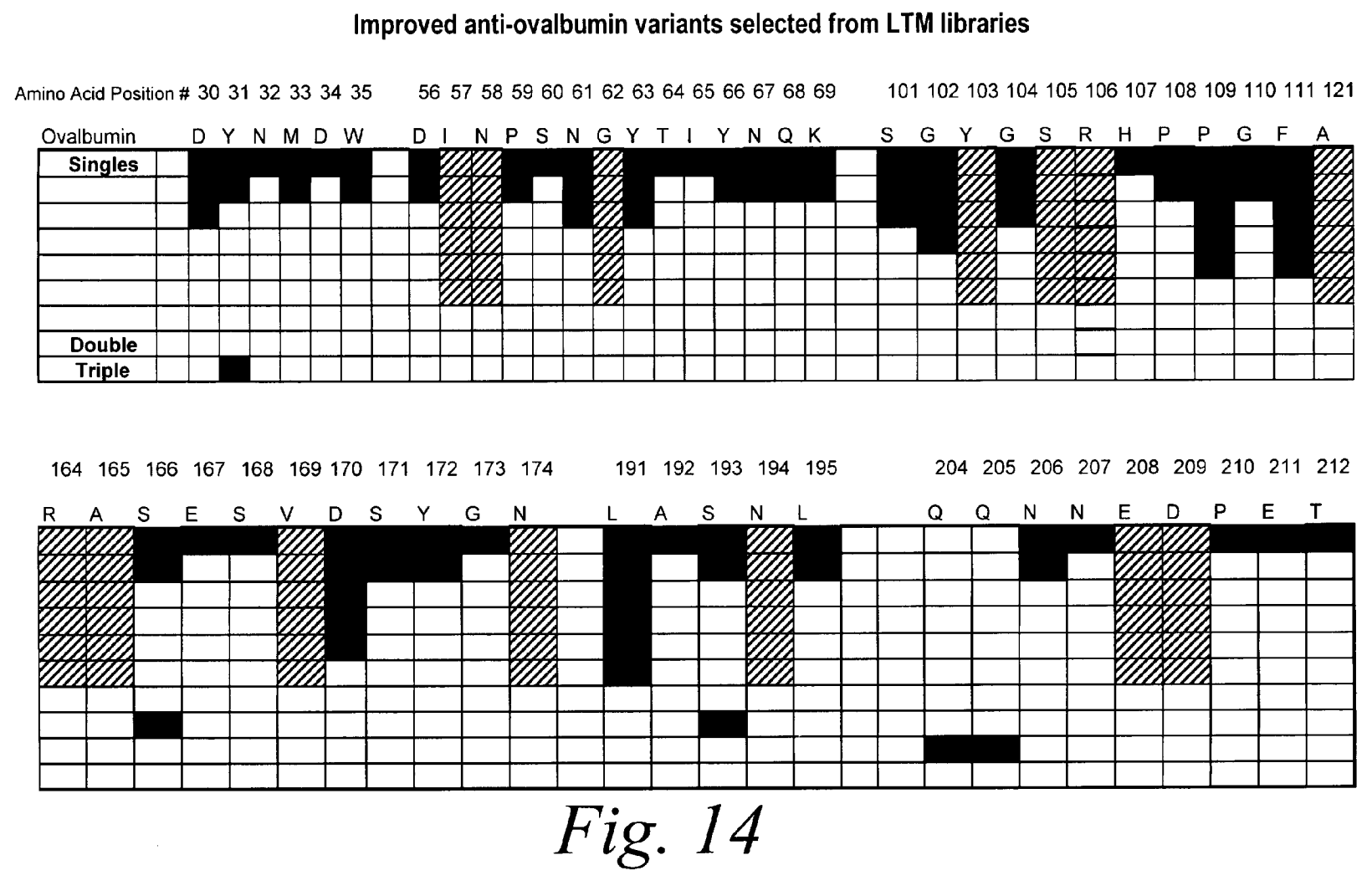

Accordingly, the recovered enhanced antigen binding mutations in each CDR after mutagenesis of all CDRs by each of the nine different amino acids tested was arrayed and results are shown in FIG. 14. Each CDR was determined to also display at least one position in which no mutations were found, e.g., Ile57, Asn58, and Gly62 positions of $V_H$ CDR2, positions Tyr103, Ser105, Arg106 and Ala121 of $V_H$ CDR3 region. For $V_L$ positions; R164, A165, V169 and N174 of CDR1, N194 of CDR2, E208 and D209 of CDR3 were found not to be replaced after extensive screening. These results indicate that in addition to the "hot spot" replacement positions and any type of preferred amino acid recovered as described above, there are also "cold spot" CDR positions. The "cold spot" positions indicate that any of the substitutions either confer no antigen binding advantage or imparted inferior binding properties.

Example 5

Methods for Conducting Combinatorial Beneficial Mutagenesis

In this example, methods for conducting combinatorial beneficial mutagenesis, are described.

Briefly, the method incorporates the beneficial mutations found using LTM, and combines them together into a single library. Therefore, synergistic effects of multiple mutations can be explored in this process. This combinatorial approach resembles the WTM method except that the selected codon substitutions within the CDRs are the different beneficial amino-acid substitutions identified by LTM. Thus, not every residue position in an antibody CDR will contain a mutation, and some positions will have multiple different amino acids substituted at that position. Overall, many if not all, combinations of beneficial mutations within a CDR or an antibody chain will be represented by at least one of the coding sequences in the library. As will be seen below, this coding-sequence library can be prepared by a modification of the WTM method, except that instead placing codons for a single amino acid at each different position in the variable coding region, the codons that are introduced are those corresponding to all beneficial mutations detected in the LTM method.

In this example, a combinatorial beneficial heavy chain CDR1 library is constructed using the improved anti-ovalbumin variants described in FIG. 14. The first amino acid position 30, encodes (at minimum) Asp (wild-type) and Lys; position 31, Tyr and Lys; position 32 Asn and Tyr; position 33 Met, His, and Lys; position 34 Asp and Pro; position 35 Trp and Lys. The DNA sequence is represented by a degenerate CDR1 oligonucleotide that incorporates the combinatorial beneficial mutations identified from the LTM analysis (Table 1).

TABLE 1

| Nucleotide base possibilities from 5' to 3' | | | | | | | | | | | | | | | |
|---|---|---|---|---|---|---|---|---|---|---|---|---|---|---|---|
| 5' | G | A | C | T | A | C | A | A | C | A | T | G | G | A | C | T | G | G | 3' |
| | A | | G | A | | G | T | | | C | A | C | C | C | | A | A | G |

A similar process can be performed with all CDR loops to produce a 6-CDR beneficial library, or sub-libraries can be produced and screened in combination. For example, if the library size is too large to be screened in a single library, then smaller sub libraries can be produced. For example, a 3-CDR heavy chain library and a 3-CDR light chain library can be produced for greater efficiencies. After screening, the beneficial mutations of the heavy and light chain libraries can be further combined into a single library that incorporates mutations in the appropriate loops.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method of distinguishing one or more functional amino acid residues from non-functional amino acid residues within a polypeptide comprising:
   selecting one or more amino acid residues within the amino acid sequence of the polypeptide;
   determining an amino acid residue to be substituted for the one or more amino acid residues selected;
   synthesizing polynucleotides encoding the polypeptide or portion thereof comprising the selected amino acid residues, the polynucleotides collectively representing possible variant amino acid substitutions according to the following criteria:
   i) each polynucleotide containing at each codon position in the defined region, either a codon required for the synthesis of the amino acid residue of the polypeptide or a codon for one of the predetermined amino acid residues, and
   ii) each polynucleotide containing no more than one codon for the predetermined amino acid residue,
   thereby generating an expression library containing the polynucleotides;
   expressing the expression library to produce polypeptide analogs; and
   screening the polypeptide analogs for an alteration in a measurable property such that one or more functional amino acid residues(s) within the polypeptide, or portion thereof, is identified as contributing to the measurable property and therefore distinguished from a non-functional amino acid residue, wherein the functional amino acid residue(s) identified as contributing to a measurable property is determined to be suitable for mutagenesis and the non-functional residue(s) is determined to be unsuitable for mutagenesis, and wherein one or more functional amino acid residues(s) are exclusively mutagenized.

2. The method of claim 1, wherein the mutagenesis is selected from the group consisting of look-through mutagenesis (LTM), walk-through mutagenesis (WTM), or a combination thereof.

3. The method of claim 1, wherein the polypeptide is an antibody or fragment thereof.

4. The method of claim 3, wherein the measurable property is selected from the group consisting of binding specificity, binding avidity, binding affinity, Fc receptor binding, glycosylation, complement binding, half-life stability, solubility, thermal stability, catalytic activity, and enzymatic activity.

5. The method of claim 1, wherein the method further comprises the step of identifying a polynucleotide that encodes a selected polypeptide analog having an alteration in a measurable property.

6. The method of claim 5, wherein the alteration in a measurable property is an enhanced property.

7. The method of claim 6, wherein the enhanced property is high affinity antigen binding.

8. The method of claim 7, wherein the antigen is a therapeutic target in a human disease or disorder.

9. The method of claim 1, wherein the screening comprises, contacting a polypeptide with a target substrate, the polypeptide being associated with the polynucleotide encoding the polypeptide, the polynucleotide or polypeptide being associated with a detectable moiety, such that a variant polypeptide capable of binding a target substrate is detected and thereby identified as encoded by the polynucleotide.

10. The method of claim 9, wherein the detectable moiety is selected from the group consisting of a biotin moiety, a GST moiety, a myc immunotag moiety, and a His tag moiety.

11. The method of claim 9, wherein the polynucleotide is associated with the polypeptide analog using expression display selected from the group consisting of ribosome display, polysome display, phage display, prokaryotic (bacterial) display, yeast display, eukaryotic cell display, and arrayed library display.

12. The method of claim 1, wherein the polypeptide is a single chain antibody (sFVs).

13. The method of claim 1, wherein the defined region comprises a CDR or portion thereof selected from the group consisting of CDR1, CDR2, CDR3, CDR4, CDR5, CDR6 and a combination thereof.

14. The method of claim 1, wherein the predetermined amino acid residue is selected from the group consisting of Ser, Thr, Asn, Gln, Tyr, Cys, His, Glu, Asp, Lys Arg, Ala, Gly, Ile, Leu, Met, Phe, Pro, Trp and Val.

* * * * *